United States Patent [19]
Noel et al.

[11] Patent Number: 5,304,161
[45] Date of Patent: Apr. 19, 1994

[54] ABSORBENT ARTICLE HAVING RAPID ACQUIRING, MULTIPLE LAYER ABSORBENT CORE

[75] Inventors: John R. Noel; Nicholas A. Ahr, both of Cinncinati, Ohio

[73] Assignee: The Procter & Gamble Company, Cincinnati, Ohio

[21] Appl. No.: 931,122

[22] Filed: Aug. 17, 1992

Related U.S. Application Data

[63] Continuation of Ser. No. 637,090, Jan. 3, 1991, abandoned.

[51] Int. Cl.$^5$ .................. A61F 13/15; A61F 13/20
[52] U.S. Cl. ........................... 604/378; 604/358; 604/368; 604/385.1
[58] Field of Search ............... 604/358, 365, 368, 369, 604/378, 385.1, 366, 370, 375

[56] References Cited

U.S. PATENT DOCUMENTS

| | | |
|---|---|---|
| 1,946,626 | 2/1934 | Jurgensen . |
| 2,296,341 | 9/1942 | Fourness ............................ 604/378 |
| 3,386,442 | 6/1968 | Sabee . |
| 3,406,688 | 10/1968 | Cubitt . |
| 3,431,911 | 3/1969 | Meisel, Jr. ...................... 604/369 |
| 3,528,421 | 9/1970 | Vaillancourt et al. . |
| 3,572,342 | 3/1971 | Lindquist et al. . |
| 3,604,422 | 9/1971 | Sabee . |
| 3,651,809 | 3/1972 | Champaigne, Jr. ................. 604/368 |
| 3,695,269 | 10/1972 | Malaney . |
| 3,799,167 | 3/1974 | Miller et al. . |
| 3,815,602 | 6/1974 | Johns et al. ......................... 604/366 |
| 3,825,006 | 7/1974 | Ralph . |
| 3,838,693 | 10/1974 | Sherman . |
| 3,871,037 | 3/1975 | Willington . |
| 3,954,721 | 5/1976 | Gross . |

(List continued on next page.)

FOREIGN PATENT DOCUMENTS

| | | |
|---|---|---|
| 0339461 | 11/1989 | European Pat. Off. . |
| 0343941 | 11/1989 | European Pat. Off. . |
| 0397110A2 | 11/1990 | European Pat. Off. . |
| 0399564A | 11/1990 | European Pat. Off. . |
| 0414541 | 2/1991 | European Pat. Off. . |
| WO91/11163 | 8/1991 | PCT Int'l Appl. . |
| WO91/11164 | 8/1991 | PCT Int'l Appl. . |
| 2078527 | 1/1962 | United Kingdom . |
| 9111162 | 8/1991 | World Int. Prop. O. .......... 604/378 |

*Primary Examiner*—Randall L. Green
*Assistant Examiner*—P. Zuttarelli
*Attorney, Agent, or Firm*—Jeffrey V. Bamber; Steven W. Miller; E. Kelly Linman

[57] ABSTRACT

An absorbent article, such as a disposable diaper, adult incontinent pad, sanitary napkin, and the like, is disclosed which has a rapid acquiring, multiple layer absorbent core. The absorbent article may be in an improved shape that can be worn in the wearer's usual undergarments. The absorbent article of the present invention comprises a liquid pervious topsheet, a liquid impervious backsheet, and a multiple layer absorbent core positioned between the topsheet and the backsheet. The multiple layer absorbent core comprises at least one rapid acquiring acquisition/distribution layer and at least one storage layer positioned subjacent each acquisition layer. The acquisition/distribution layers have a fluid acquisition/distribution rate of at least about 2 cubic centimeters of synthetic urine per second when tested under a pressure of about 28 grams per square centimeter. The storage layers at least partially comprise a "high-speed" absorbent gelling material which is capable of reaching at least about 40% of its absorptive capacity in less than or equal to about 10 seconds. A multiple layer absorbent core for an absorbent article is also disclosed.

10 Claims, 4 Drawing Sheets

U.S. PATENT DOCUMENTS

| | | | |
|---|---|---|---|
| 3,983,095 | 9/1976 | Bashaw et al. | |
| 3,996,936 | 12/1976 | Widlund et al. | 604/364 |
| 4,136,697 | 1/1979 | Smith | |
| 4,211,227 | 7/1980 | Anderson et al. | 604/380 |
| 4,231,357 | 11/1980 | Hessner | 128/156 |
| 4,285,342 | 8/1981 | Mesek | |
| 4,335,722 | 6/1982 | Jackson | |
| 4,338,371 | 7/1982 | Dawn et al. | 604/378 |
| 4,397,644 | 8/1983 | Matthews et al. | 604/378 |
| 4,410,324 | 10/1983 | Sabee | |
| 4,411,660 | 10/1983 | Dawn et al. | 604/368 |
| 4,500,315 | 2/1985 | Pieniak et al. | |
| 4,536,181 | 8/1985 | Cook | |
| 4,537,590 | 8/1985 | Peiniak et al. | |
| 4,557,777 | 12/1985 | Sabee | |
| 4,655,757 | 4/1987 | McFarland et al. | |
| 4,666,439 | 5/1987 | Williams et al. | |
| 4,676,784 | 6/1987 | Erdman et al. | |
| 4,685,914 | 8/1987 | Holtman | 604/385.1 |
| 4,699,823 | 10/1987 | Kellenberger et al. | |
| 4,798,603 | 1/1989 | Meyer et al. | |
| 4,888,093 | 12/1989 | Dean et al. | 604/375 |
| 4,888,238 | 12/1989 | Katz et al. | |
| 4,900,318 | 2/1990 | Toth | |
| 4,911,700 | 3/1990 | Makoui et al. | 604/375 |
| 4,923,454 | 5/1990 | Seymour et al. | |
| 4,935,022 | 6/1990 | Lash et al. | |
| 4,950,262 | 8/1990 | Takagi | |
| 4,988,344 | 1/1991 | Reising et al. | 604/368 |
| 4,990,147 | 2/1991 | Freeland | |
| 5,013,309 | 5/1991 | Baigas, Jr. et al. | 604/385.1 |
| 5,037,409 | 8/1991 | Chen et al. | |
| 5,061,259 | 10/1991 | Goldman et al. | |
| 5,061,260 | 10/1991 | Callahan et al. | |
| 5,079,004 | 1/1992 | Black et al. | 604/378 |
| 5,098,422 | 3/1992 | Davis et al. | 604/358 |
| 5,147,343 | 9/1992 | Kellenberger | 604/368 |
| 5,147,345 | 9/1992 | Young et al. | 604/358 |
| 5,149,335 | 9/1992 | Kellenberger et al. | |
| 5,192,606 | 3/1993 | Proxmire et al. | 604/378 |

ABSORBENT ARTICLE HAVING RAPID ACQUIRING, MULTIPLE LAYER ABSORBENT CORE

This is a continuation of application Ser. No. 07/637,090, filed on Jan. 3, 1991, now abandoned.

FIELD OF THE INVENTION

This invention relates to absorbent articles, such as disposable diapers, incontinent articles, sanitary napkins and the like, having multiple layer absorbent cores. This invention also relates to a rapid acquiring, multiple layer absorbent core for an absorbent article and to an absorbent article, such as an adult incontinent pad, which when provided with such an absorbent core, may be in an improved shape that can be worn in the wearer's usual

BACKGROUND OF THE INVENTION

Absorbent articles such as disposable diapers, adult incontinent pads, sanitary napkins and the like come in many different sizes and shapes. Diapers and incontinent pads are generally garments worn by infants or incontinent persons that are drawn up between the legs and fastened about the waist of the wearer. Sanitary napkins are designed to receive and contain vaginal discharges, such as menses, and are typically held adjacent to the human body through the agency of a garment, such as an undergarment or a panty, or a specially designed belt.

There is a continual effort to make such absorbent articles more comfortable and discrete and less obtrusive for the wearer. This is particularly true in the case of adult incontinent pads. Adult incontinent pads, by their nature, have previously been made fairly thick so they can handle the relatively large quantities of body exudates, such as urine, they receive. The desire for less bulky incontinent pads is particularly great among incontinent persons, many of whom are elderly adults, because it can be embarrassing to wear diaper-like articles. In addition, most individuals would rather use some type of article that could be worn with the undergarments they normally wear.

One key component of an absorbent article that contributes to its size and bulk is the absorbent body used therein. Typically, absorbent articles comprise a liquid pervious material that faces the wearer's body, a liquid impervious material that faces the wearer's clothing, and an absorbent body or absorbent core that is sandwiched between the liquid pervious material and the liquid impervious material. In prior absorbent articles, a material comprising comminuted wood pulp, referred to as airfelt, was used in the absorbent core to serve the functions of acquiring, distributing, and storing liquids and other exudates deposited on the surface of the absorbent article. One of the disadvantages of using airfelt was that a thick layer of airfelt had to be used to obtain the needed capacity.

Recent attempts to improve the effectiveness of absorbent cores have included distributing particles of absorbent gelling material throughout or in portions of the absorbent core. Some of these improvements are described in U.S. Pat. No. 4,610,678 issued to Paul T. Weisman and Stephen A. Goldman on Sep. 9, 1986; U.S. Pat. No. 4,673,402 issued to Paul T. Weisman, Dawn I. Houghton, and Dale A. Gellert on Jun. 16, 1987; and European Patent Application EP-A-254,476 assigned to The Procter & Gamble Company, published Jan. 27, 1988, the disclosures of which are incorporated by reference herein. Another improvement to the effectiveness of absorbent cores is described in U.S. Pat. No. 4,781,711 issued on Nov. 1, 1988 to Dawn I. Houghton and Nicholas A. Ahr, the disclosure of which is also incorporated by reference herein. While the absorbent articles described in the above references work quite well, the search for improved absorbent articles that are capable of rapidly and efficiently absorbing increasingly greater quantities of exudates has continued.

The structure of the absorbent core ideally should be such that the absorbent article absorbs exudates immediately when they are discharged so that such exudates will not pool or otherwise remain on top of the core. The absorbent core ideally should also be constructed so exudates initially absorbed will be immediately transported to a place within the absorbent core where they can be stored. One problem with many of the prior absorbent articles that used absorbent gelling materials is that the absorbent gelling materials do not absorb liquid exudates as fast as they are deposited on the core. Slow absorbing absorbent gelling materials, thus, do little to increase the immediately available capacity of the core. Such absorbent gelling materials typically require several seconds or minutes to absorb fluids.

The absorbent core should also provide a system of distribution and storage for exudates that efficiently uses the entire capacity of the absorbent core. One problem that often arises in absorbent articles without such a system (particularly those absorbent articles that use the same layer or batt of material to serve the different functions of acquiring, distributing, and storing exudates) is that the storage capacity of the absorbent article is exhausted prematurely. This can occur in several different ways. In many absorbent articles, the saturation of the absorbent material in the region where exudates are initially deposited reduces the ability of the absorbent material to transport additional exudates to other parts of the core. This phenomenon can also lead to the undesirable pooling of exudates on top of the core discussed above.

In other absorbent articles the effectiveness of absorbent cores containing particles of absorbent gelling material can be adversely affected by a phenomenon called "gel blocking". The term "gel blocking" describes a situation that occurs when a particle of absorbent gelling material is wetted and the surface of the particle swells so as to inhibit liquid transmission into the interior of the absorbent core. Wetting of the interior of the absorbent core, therefore, takes place via a very slow diffusion process. In practical terms, this means that acquisition of liquid by the absorbent core is much slower than the discharge of the liquids to be absorbed, and leakage from the absorbent article may take place well before the particles of absorbent gelling material in the absorbent core are fully saturated or before the liquid can diffuse or wick past the "blocking" particles into the rest of the absorbent core.

Therefore, a need exists for an absorbent article of an improved shape that has an absorbent core that quickly acquires and distributes exudates throughout the absorbent core where they can be stored.

It is an object of the present invention to provide an absorbent article, particularly an incontinent article, of an improved shape that can be worn in the wearer's usual undergarments.

It is another object of the present invention to provide an absorbent core for an absorbent article which is especially efficient in acquiring, distributing, and storing exudates as they are deposited on the absorbent article.

In particular, it is an object of the present invention to provide an absorbent core that has a system in which the functions of acquiring and distributing exudates are handled by layers that are separate from the layers used for storing exudates. Ideally, such a system will allow exudates to be continuously acquired and distributed to storage layers by layers that are not subject to the prior problems of saturation and gel blocking.

These and other objects of the present invention will be more readily apparent when considered in reference to the following description and when taken in conjunction with the accompanying drawings.

SUMMARY OF THE INVENTION

The present invention provides absorbent articles, such as disposable diapers, incontinent pads, sanitary napkins and the like that have multiple layer absorbent cores that are capable of acquiring and containing liquids in an especially effective and efficient manner. In one embodiment, the absorbent articles of the present invention can be in an elongated-pear shape that can be worn in the wearer's undergarments.

The absorbent articles of the present invention comprise a liquid pervious topsheet, a liquid impervious backsheet joined with the topsheet, and an absorbent core positioned between the topsheet and the backsheet. The absorbent core of the present invention comprises multiple layers. The multiple layers comprise at least one pair of layers. In each pair of layers, the uppermost layer is a rapid acquiring exudate acquisition/distribution layer (typically a low density web or batt of material). A storage layer comprised at least partially of a high-speed absorbent gelling material is positioned subjacent each acquisition/distribution layer.

The acquisition/distribution layers have a fluid acquisition/distribution rate of at least about 2 cubic centimeters of synthetic urine per second when the acquisition/distribution layer is tested according to the Fluid Acquisition/Distribution Test under a pressure of about 28 grams per square centimeter. The acquisition/distribution layers in at least some embodiments will comprise a "low density" web or batt of material, such as a nonwoven web, with a density of less than or equal to about 0.1 grams per cubic centimeter and a basis weight of from about 17 to about 270 grams per square meter, when the acquisition/distribution layers are placed under a load of 0.1 psi (7 grams per square centimeter).

The storage layers are comprised at least partially of a "high-speed" absorbent gelling material. A "high-speed" absorbent gelling material is an absorbent gelling material which reaches at least about 40% of its absorptive capacity in less than or equal to about 10 seconds. Preferably, this will be a material that has a total capacity of at least about 25 times its dry weight in fluid, such as synthetic urine, and a liquid acquisition rate of greater than or equal to about 0.8 grams of synthetic urine per second per gram of such material. Preferably, the storage layers each have a basis weight of between about 20 to about 1,200 grams/square meter and a density of less than or equal to about 0.2 grams per cubic centimeter.

In use, it is believed that the exudate acquisition/distribution layer is capable of quickly taking exudates into itself as they are deposited on the absorbent article and distributing such exudates to the lower storage layer in a manner that substantially reduces or eliminates prior problems of saturation of the materials adjacent the zone of exudate application and gel blocking. It is believed that the combination of the layers of the particular materials used provides a structure that is also capable of quickly storing the absorbed liquids.

While not wishing to be bound by any particular theory, it is believed that the multiple layer absorbent core distributes exudates by a cascading effect. It is believed that the manner of acquisition, distribution, and storage of the multiple layer absorbent core can be analogized to the filling of an ice cube tray with water in that when one region of the absorbent core is filled, exudates will quickly flow laterally to the sides of the filled region to begin filling other unfilled regions.

The present invention also relates to multiple layer absorbent cores that can be employed in absorbent articles of other sizes and shapes.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

1. Overall Characteristics of the Absorbent Article

The overall characteristics of the absorbent article of the present invention will be discussed first.

Figure 1:
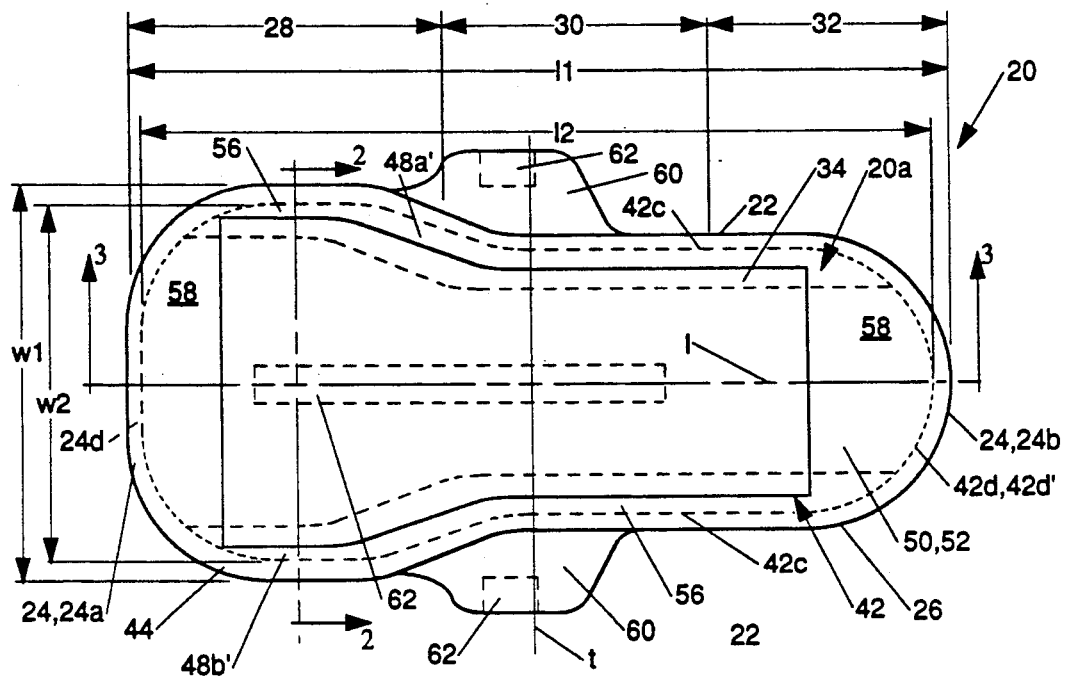
FIG. 1 is a plan view of a preferred embodiment of the absorbent article of the present invention.
Figure 2:
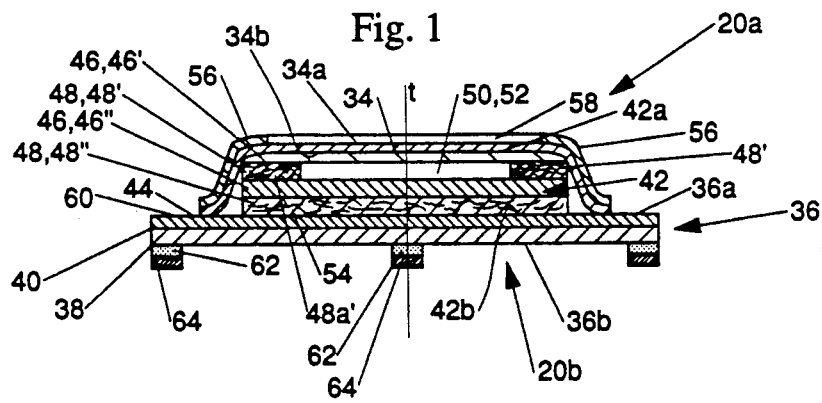
FIG. 2 is an enlarged transverse sectional view of the absorbent article of the present invention taken along line 2—2 of FIG. 1.
Figure 3:
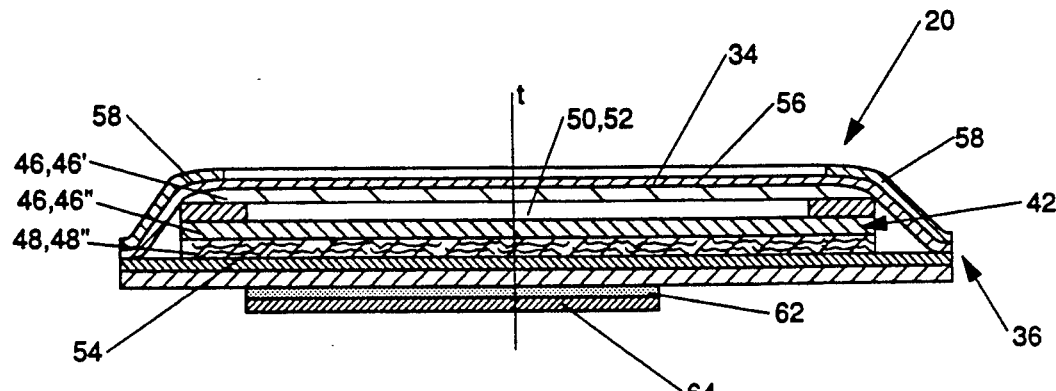
FIG. 3 is a longitudinal sectional view of the absorbent article of the present invention taken along line 3—3 of FIG. 1.

FIGS. 1-3 show a preferred embodiment of a disposable absorbent article of the present invention. The absorbent article of the present invention shown in the drawings is of an improved shape that can fit into the wearer's undergarments. The absorbent article has a multiple layer absorbent core that is capable of quickly acquiring, distributing, and storing body exudates.

As used herein, the term "absorbent article" refers to articles which absorb and contain body exudates. More specifically, the term refers to articles which are placed against or in proximity to the body of the wearer to absorb and contain the various exudates discharged from the body. The term "absorbent article" is intended to include diapers, incontinent articles, sanitary napkins, and the like. The term "incontinent articles" is intended to include pads, undergarments (pads held in place by a suspension system of some type, such as a belt, or the like), inserts for absorbent articles, capacity boosters for absorbent articles, briefs, bed pads, and the like, regardless of whether they be worn by adults or other incontinent persons. The term "disposable" refers to articles which are intended to be discarded after a single use. That is, disposable articles are not intended to be laundered or otherwise restored or reused.

In the preferred embodiment illustrated, the absorbent article is an adult incontinent pad (or "pad") designated 20. (It should be understood that even though the preferred embodiment is illustrated and described in the form of an incontinent pad, the description of the various component parts of the incontinent pad 20 will also apply generally to other types and shapes of absorbent articles that are made according to the present invention.)

The incontinent pad 20 has two surfaces, a body-contacting surface or "body surface" 20a and a garment surface 20b. The incontinent pad 20 is shown in FIG. 1 as viewed from its body surface 20a. The body surface 20a is intended to be worn adjacent to the body of the wearer. The garment surface 20b of the incontinent pad 20 (shown in FIG. 2) is on the opposite side and is intended to be placed adjacent to the wearer's undergarments when the incontinent pad 20 is worn.

The incontinent pad 20 has two centerlines, a longitudinal centerline l and a transverse centerline t. As used herein the term "longitudinal" refers to a line, axis or direction in the plane of the incontinent pad 20 that is generally aligned with (e.g., approximately parallel to) a vertical plane that bisects a standing wearer into left and right body halves when the incontinent pad 20 is worn. The term "transverse" refers to the line, axis or direction generally perpendicular to the longitudinal direction which lies within the plane of the incontinent pad 20. The incontinent pad 20 has a longitudinal dimension that runs in the general direction of the longitudinal centerline l, and a transverse dimension that runs in the general direction of the transverse centerline t. The incontinent pad 20 is typically longer in the longitudinal dimension than in the transverse dimension.

FIG. 1 shows that the incontinent pad 20 has two spaced apart longitudinal edges 22 and two spaced apart transverse or end edges (or "ends") 24, which together form the periphery 26 of the incontinent pad 20. When the incontinent pad 20 is worn, one of the end edges 24 will be oriented toward the front of the wearer, and one of the end edges 24 will be oriented toward the rear of the wearer. The end edge 24 oriented toward the front of the wearer, the "front end edge", is designated 24a, and the end edge oriented toward the rear of the wearer, the "rear end edge" or "back end edge", is designated 24b.

The shape of the absorbent article 20 of the present invention in plan view is shown in FIG. 1. While the absorbent article 20 may have any shape known in the art, the preferred embodiment of the absorbent article, incontinent pad 20, shown in FIG. 1 is symmetrical about its longitudinal centerline l, but is asymmetrical about its transverse centerline t. The absorbent article 20 can be divided into three regions in plan view: a first end region 28, a central region 30, and a second end region 32.

The first end region 28 is intended to be to the front of the wearer's body when the incontinent pad 20 is worn. The second end region 32 is intended to be to the wearer's rear when the incontinent pad 20 is worn. The central region 30 lies between the first and second end regions, and is intended to be worn in the area of the wearer's crotch. The first end region 28 and the second end region 32 extend outwardly from the central region 30 toward the ends 24a and 24b respectively, a distance of about ⅛ to about ⅓ of the total length of the incontinent pad 20; although the exact size of the first and second end regions will vary according to the precise design and intended positioning of the incontinent pad 20.

The shape of the longitudinal edges 22 of the incontinent pad 20 in the first end region 28 is defined by curved convex outward (or outwardly arcuate with relation to each other) lines on each side of the longitudinal centerline l. The lines that form the longitudinal edges 22 change direction of curvature and curve inward toward each other in at least a portion of the central region 30. The longitudinal side edges 22 are generally straight and parallel to each other in the second end region 32 in the embodiment shown in FIGS. 1-3. In alternative embodiments, the longitudinal side edges 22 could be inwardly tapered toward the longitudinal centerline l in the second end region 32 so that the longitudinal side edges 22 become closer together near the rear end edge 24b of the incontinent pad 20 than they are adjacent the central region 30. The end edges 24 of the incontinent pad 20 are rounded and curved convex outwardly.

The overall shape of the incontinent pad 20 shown in FIG. 1 could be described in a number of ways. The incontinent pad 20 could be said to be dog bone-shaped or hourglass-shaped on one side of the transverse centerline t, and could be said to have longitudinal side edges on the other side of the transverse centerline t that are either approximately parallel to each other or inwardly tapered. Alternatively, the incontinent pad 20 could be viewed as being of an elongated pear-shape.

There are several reasons for providing an incontinent pad in such a shape. The first end region 28 of the incontinent pad 20 is worn to the wearer's front. This is the area in which the wearer's genitals are located, and thus, where urine is typically deposited. The first end region 28 of the incontinent pad 20 has been made larger than the other regions of the pad to provide a large target to receive this urine. The central region 30 is made narrower than the first end region 28 so the incontinent pad 20 will fit comfortably between the wearer's legs and will accommodate the wearer's movements. The second end region 32 is narrower than the widest portion of the first end region 28 so that there will be less tendency for the second end region 32 to buckle and wedge in the crevice of the user's body between the buttocks.

The dimensions of the preferred incontinent pad 20 shown in FIG. 1 are as follows. The incontinent pad 20 has an overall length $l_1$ of about 35 centimeters (cm.). The overall width of the pad 20 $w_1$ at its widest portion (in the first end region 28, not including the span of the optional side flaps 60 described below) is about 16 cm. The overall length $l_2$ of the absorbent core 42 of the incontinent pad 20 is about 33 cm. The overall width $w_2$ of the absorbent core 42 at its widest portion is about 14 cm. The width of the absorbent core 42 narrows to about 9 cm. in the central region 30 at the transverse centerline t, and to about 8.5 cm. in the second end region 32. The latter dimension is measured inboard, i.e., toward the intersection of the longitudinal and transverse centerlines 1 and t, of the place where the curvature of the end edge 24b of the incontinent pad 20 begins. In addition, as shown in FIG. 1, the topsheet 34 and the backsheet 36 extend outward away from the intersection of the longitudinal and transverse centerlines 1 and t to form a border 44 approximately 1 cm. wide around the circumference of the absorbent core 42. The incontinent pad 20 has a surface area of approximately 55 square inches (about 355 $cm^2$), and is much smaller than traditional diaper-like incontinent briefs.

It should be understood, however, that the above dimensions are preferred for the particular embodiment of the incontinent pad 20 shown in FIGS. 1-3. The multiple layer absorbent core 42 of the present invention can be used in other types of absorbent articles and can be in many other shapes and sizes depending on the type of absorbent article and the absorbent capacity needed.

FIG. 2 shows the individual components of the incontinent pad 20. The incontinent pad 20 of the present invention generally comprises three primary components. These include a liquid pervious topsheet 34, a liquid impervious backsheet 36, and a multiple layer absorbent core 42. The absorbent core 42 is positioned between the topsheet 34 and the backsheet 36. There are two basic types of layers in the absorbent core 42, acquisition/distribution layers 46, comprised of a low density (or "high loft") material capable of rapidly taking in and distributing exudates, and storage layers 48 comprised at least partially of a high-speed absorbent gelling material.

The layers of the absorbent core 42 are arranged in pairs so that an acquisition/distribution layer 46 is always on top of a storage layer 48 (that is, the acquisition/distribution layer 46 in issue is always positioned between the topsheet 34 and the underlying storage layer 48). In the embodiment shown in FIGS. 1-3, the absorbent core 42 comprises four layers. As shown in FIG. 2, the four layers comprise from the top of the absorbent core 42 to the bottom: a first acquisition/distribution layer 46', a first storage layer 48', a second acquisition/distribution layer 46" and a second storage layer 48".

The incontinent pad 20 of the present invention can also be provided with any optional additional components that are known in the art. The optional components may include one or more longitudinal barrier shields 56 (shown in FIG. 1), one or more transverse barrier shields 58 (also shown in FIG. 1), side flaps or "wings" 60 (FIGS. 1 and 2), an adhesive fastening means 62 (FIG. 2), and a removable cover strip or release liner 64 (FIG. 2). In the embodiment shown in FIG. 2, the incontinent pad 20 of the present invention is provided with one longitudinal barrier shield 56 along each longitudinal edge 22 of the pad, and one transverse barrier shield 58 along each end edge 24 of the pad. The side flaps or "wings" 60 may be at least partially folded around the crotch portion of the wearer's undergarments. The adhesive fastening means 62 serves as a means for attaching the incontinent pad 20 to the wearer's undergarments. The removable release liner 64 covers the adhesive fastening means 62 in order to keep the adhesive from becoming contaminated or sticking to a surface other than the crotch portion of the undergarment prior to use.

In the following sections of this description, the characteristics of the individual components are discussed in greater detail in Section 2. The optional components of the incontinent pad 20 are discussed in Section 3. The alternative embodiments of the absorbent article are discussed in Section 4. The test methods used herein are described in Section 5.

2. The Individual Components of the Absorbent Article

Looking at the components of the incontinent pad 20 more specifically, FIG. 2 shows the liquid pervious topsheet (or simply the "topsheet") 34 overlies the other components of the incontinent pad 20 (other than the barrier shields). The topsheet 34 is oriented towards and contacts the body of the wearer. The topsheet 34 is the portion of the incontinent pad 20 that initially receives bodily discharges. The topsheet 34 has a body-facing side (or "body surface") 34a and a core-facing side 34b. The body-facing side 34a of the topsheet 34 generally forms at least a portion of the body-contacting surface ("body surface") 20a of the incontinent pad 20.

The topsheet 34 should permit liquids to readily transfer through its thickness toward the absorbent core 42. The topsheet 34 should, therefore, be liquid pervious. The topsheet 34 should also be flexible and nonirritating to the wearer's skin. As used herein the term "flexible" refers to materials which are compliant and readily conform to the shape of the body or respond by easily deforming in the presence of external forces. Preferably the topsheet 34 is not noisy, to provide discretion for the wearer. The topsheet 34 should be clean in appearance and somewhat opaque to hide the bodily discharges collected in and absorbed by the absorbent components. The topsheet 34 should further exhibit good strikethrough and a reduced tendency to rewet, permitting bodily discharges to rapidly penetrate the topsheet 34 and make their way to the the absorbent core 42, but not allowing such discharges to flow back through the topsheet 34 to the skin of the wearer.

A suitable topsheet 34 may be made from a number of different materials, such as porous foams, reticulated foams, apertured plastic films, natural fibers (e.g., wood or cotton fibers), synthetic fibers (e.g., polyester or polypropylene fibers), or from a combination of natural or synthetic fibers. Preferably, the topsheet is made of a hydrophobic material to isolate the wearer's skin from liquids in the absorbent core 42.

There are a number of manufacturing techniques which may be used to manufacture the topsheet 34. For example, the topsheet 34 may be woven, nonwoven (e.g., spunbonded, carded or the like), foamed, or cast. A preferred topsheet 34 is spunbonded and thermally bonded by means well-known to those skilled in the fabric art. Preferably, the topsheet has a weight from about 18 to about 30 grams per square meter, a minimum dry tensile strength of at least about 400 grams per centimeter in the machine direction and a wet tensile strength of at least about 55 grams per centimeter in the cross-machine direction.

The backsheet 36 is shown in FIG. 2. The backsheet 36 is the component of the incontinent pad 20 that prevents the exudates from wetting articles which contact the incontinent pad 20. Typically, the articles which come in contact with the incontinent pad 20 would be the wearer's undergarments. The present invention is also concerned, however, with keeping the wearer's body and clothing free from soiling.

The backsheet 36 has a core-facing side 36a and a garment side 36b. At least a portion of the core-facing side 36a of the backsheet 36 will ordinarily face the core 42. It is also within the scope of the present invention for portions of the core-facing side 36a of the backsheet 36 (such as wings 60) to be folded so that they may not necessarily always face the core 42. However, the core-facing side 36a of the backsheet 36 can be distinguished from the garment side 36b of the backsheet 36 because the core-facing side 36a is the side of the backsheet 36 that is joined to the topsheet 34 and adjacent to the core 42. The garment side 36b of the backsheet 36 generally forms the garment surface 20b of the incontinent pad 20.

The backsheet 36 may be any flexible, liquid impervious material that prevents discharges collected by the incontinent pad 20, (particularly discharges which may not be completely absorbed by the core 36), from escaping the incontinent pad 20 and soiling the undergarments and clothing of the wearer. Preferably, the backsheet 36 is not noisy, to provide discretion for the wearer. The backsheet 36 may also be impervious to malodorous gases generated by bodily discharges, so that the malodors do not escape and become noticed by the wearer and others. In other alternatives, the backsheet 36 may be pervious to water vapor (but not to liquids) so that any such vapors trapped between the incontinent pad 20 and the wearer's skin can escape to make the product more comfortable to wear.

Preferably, at least a portion of the backsheet 36 is manufactured from a thin plastic film, although other suitable liquid impervious materials may also be used. In one preferred embodiment, the backsheet 36 is a polyethylene film having a thickness of from about 0.012 mm (0.5 mil) to about 0.051 cm (2.0 mils), although other flexible, liquid impervious materials may be used. A suitable polyethylene film is manufactured by Monsanto Chemical Corporation and marketed in the trade as Film No. 8020. The backsheet 36 is may also be embossed and/or matte finished to provide a more cloth-like appearance.

In a most preferred embodiment, the backsheet 36 is comprised of two layers. In the embodiment shown in FIG. 2, the backsheet 36 comprises a first layer 38 of lofted material disposed on the core-facing side 36a of the backsheet 36. The purpose of the first layer 38 is to provide a comfortable, nonirritating surface against the body of the wearer. The first layer 38 may be comprised of any suitable material, such as a nonwoven material. Preferably, the first layer 38 comprises a hydrophobic nonwoven material. The second layer 40 may be disposed on the garment side 36b of the backsheet 36, and may comprise a fluid impervious film. A low density polyethylene material about 0.01 to about 0.05 millimeters in thickness, preferably about 0.02 millimeters in thickness, has been found to work well as this second layer 40. A polyethylene film, such as is sold by the Ethyl Corporation, Visqueen Division, under model XP-39385 is particularly well suited for this second layer 40. The backsheet 36 may also be made of a soft, cloth-like material which is hydrophobic relative to the topsheet 34. A polyester or polyolefinic fiber backsheet 36 has been found to work well. A particularly preferred soft, cloth-like backsheet 36 material is a laminate of a polyester nonwoven material and a film such as described in U.S. Pat. No. 4,476,180 issued to Wnuk on Oct. 9, 1984, the disclosure of which patent is hereby incorporated by reference herein.

The topsheet 34 and the backsheet 36 are joined together in any suitable manner. As used herein, the term "joined" encompasses configurations whereby the topsheet 34 is directly secured to the backsheet 36 by affixing the topsheet 34 directly to the backsheet 36, and configurations whereby the topsheet 34 is indirectly secured to the backsheet 36 by affixing the topsheet 34 to intermediate members which in turn are affixed to the backsheet 36. In a preferred embodiment, the topsheet 34 and the backsheet 36 are joined directly to each other in the periphery of the incontinent pad 20 by attachment means (not shown) such as an adhesive or any other attachment means as are known in the art. For example, a uniform continuous layer of adhesive, a patterned layer of adhesive, or an array of separate lines or spots of adhesive may be used to join the topsheet 34 to the backsheet 36.

The characteristics of the multiple layer absorbent core 42 are also shown in FIG. 2. The multiple layer absorbent core (or simply the "absorbent core", or "the core") 42 serves as a means of absorbing bodily fluids. In particular, the absorbent core 42 is the means for collecting and containing bodily discharges, such as urine, which are deposited on the core 42 or which otherwise traverse through the liquid permeable topsheet 34. The absorbent core 42 has a body-facing side 42a and a garment-facing side 42b.

The core 42 need not have a total absorbent capacity much greater than the total amount of bodily discharges to be absorbed. In the embodiment shown in FIG. 2, the core 42 is preferably made as narrow and thin as possible, so it is comfortable for the wearer. For the embodiment described herein (that is, a core used in pads designed for persons with moderate to heavy incontinence) the capacity of the core should be between about 100 to about 600 grams of synthetic urine (synthetic urine is described in Section 5 below which is entitled "Test Methods"). The core 42 can be sized and provided with different capacities to fit the use intended for the absorbent article. Thus, the core 42 may be made smaller and may have a lower absorbent capacity when it is used in incontinent pads that are intended for people with light incontinence, and when used in other types of absorbent articles, such as in diapers and sanitary napkins.

The core 42 should also be conformable and nonirritating to the wearer's skin. The core 42 should be sized to register with the topsheet 34 and backsheet 36. The core 42 is preferably positioned between the topsheet 34 and backsheet 36. The position of the core 42 prevents the absorbent material of the core 42 from shredding or becoming detached while the incontinent pad 20 is worn. The position of the core 42 also ensures proper containment of bodily discharges. The core 42 may be of any shape such as in the same general shape as the incontinent pad 20 described above, or in any other suitable shape in other embodiments. For instance, the core 42 may be rectangular or hourglass-shaped.

The absorbent core 42 preferably comprises two or more distinct layers. The preferred embodiment of the multiple layer absorbent core 42 shown in FIG. 2 comprises four layers. In the embodiment shown in FIG. 2, the four layers comprise from the top of the absorbent core 42 to the bottom: a first acquisition/distribution layer 46', a first storage layer 48', a second acquisition/distribution layer 46", and a second storage layer 48". There can be any number of pairs of acquisition/distribution layers 46 and storage layers 48 in the multiple layer absorbent core 42, from one pair of layers to a virtually infinite number of a plurality or multiplicity of pairs of layers.

There are two general requirements for the arrangement of the layers of the core 42. One requirement is that the materials be stacked so a storage layer 48 is positioned beneath an acquisition/distribution layer 46 so that the absorbed exudates will have some place to be stored. The other requirement is that when there is more than one pair of acquisition/distribution and storage layers, there must be some path through which exudates can flow to the underlying layers when the storage layers that lie above such layers become full. In the embodiment shown in FIG. 2, this flow path is provided by an aperture 52 in the first storage layer 48'.

It should be understood that for the purpose of this invention, the layers described herein refer merely to zones of the absorbent core and are not necessarily limited to single layers or sheets of material. Thus, the exudate acquisition/distribution layers 46 and the storage layers 48 may actually comprise strips of material, loose or bonded particles or fibers, laminates of material, or other combinations of such materials, such as several sheets or webs of the types of material described below. Thus, as used herein, the term "layer" also includes the terms "layers" and "layered".

The exudate acquisition/distribution layers 46 will be discussed first. The exudate acquisition/distribution layers (or simply "acquisition/distribution layers") 46 are positioned on top of the storage layers 48. The term "acquisition", as used herein refers to the ability to take in (that is, acquire into itself) exudates, particularly liquid exudates. The acquisition/distribution layers 46 may take in exudates by a number of means. The acquisition/distribution layers 46 may simply provide void space for the exudates to enter, or they may take in exudates by means such as absorption, or capillary action. The term "distribution", as used herein refers to the ability to transport exudates, particularly liquid exudates, to other areas of the absorbent article.

The exudate acquisition/distribution layers 46 serve several functions. The acquisition/distribution layers 46 should absorb exudates deposited on the absorbent article 20 (or received from the layers located above) as quickly as possible to reduce or eliminate pooling or accumulation of these exudates on top of the core 42. Preferably, the acquisition/distribution layers 46 are capable of taking in exudates at the same rate or at a rate which is faster than exudates are deposited onto the surface of the core 42. The acquisition/distribution layers 46 should also be able to transport exudates taken in to locations within the core 42 where they can be stored. Preferably, this transportation and storage is at the same or faster rate that exudates are deposited on the core 42 so that exudates will not "back up" and pool on top of the core 42 for lack of a mechanism to immediately store the same.

In addition, in the preferred embodiments of the present invention, the acquisition/distribution layers 46 and the storage layers 48 should function independently. In such embodiments, the functions of acquiring and distributing exudates may be handled nearly entirely by the acquisition/distribution layers 46, and the storage layers 48 may not be required to transport exudates to other parts of the core 42. The storage layers 48 can, as a result, be designed without taking into account any exudate distribution considerations which reduced the effectiveness of many prior disposable absorbent articles.

The acquisition/distribution layers 46 should also preferably be able to continue to function when the wearer's activities cause compressive forces to be placed on the absorbent article. The acquisition/distribution layers 46 should preferably maintain sufficient void space (or "void volume") when subjected to such forces and also when wetted so that they will be able to continue to transport liquid exudates. If this is the case, the acquisition/distribution layers will have capacity to not only handle initial gushes of liquid exudates, but will also be able to handle subsequent gushes. To maintain such void space, the acquisition/distribution layers 46 should be both dry resilient and wet resilient, and should also be moisture insensitive. The term "moisture insensitive", as used herein, refers to materials that will not collapse when wetted or otherwise be affected by the presence of moisture. A good discussion of the terms contained in this paragraph is contained in U.S. patent application Ser. No. 07/198,032 filed May 24, 1988 in the name of George S. Reising, et al., now U.S. Pat. No. 4,988,344, the disclosure of which is incorporated by reference herein.

The acquisition/distribution layers 46 are comprised of a low density (or "high loft") web or batt of material. The terms "low density" and "high loft", as used herein, refer to a batt of material having a density of less than or equal to about 0.1 grams per cubic centimeter.

The acquisition/distribution layers 46 can be comprised of a number of different types of materials. The acquisition/distribution layers 46 can be nonwoven webs of fibers, foams, or any other suitable material that provides the desired rapid fluid acquisition and distribution properties. If the acquisition/distribution layers 46 are webs of fibrous nonwoven material, they can be comprised at least partially of natural fibers (such as wood, e.g., in the form of airfelt, or cotton fibers), at least partially of synthetic fibers, (such as rayon fibers, polyester, polyethylene, polyethylene terephthalate (also known as "PET"), or polypropylene fibers), cross-linked cellulose fibers, foams, or any equivalent material or combination of materials. Suitable cross-linked cellulose fibers are described in U.S. Pat. No. 4,888,093, issued Dec. 19, 1989 to Cook, et al.; U.S. Pat. No. 4,822,543, issued Apr. 18, 1989 to Dean, et al.; U.S. Pat. No. 4,889,595, issued Dec. 26, 1989 to Schoggen, et al.; U.S. Pat. No. 4,889,596, issued Dec. 26, 1989 to Schoggen, et al.; U.S. Pat. No. 4,898,642, issued Feb. 6, 1990 to Moore, et al.; and U.S. Pat. No. 4,935,022, issued Jun. 19, 1990 to Lash, et al., the disclosures of which are incorporated by reference herein.

If the acquisition/distribution layers 46 are fibrous nonwoven webs of material, they can be comprised of fibers of any length. Preferably, however, the fibers used in the acquisition/distribution layers 46 are staple fibers. The terms "staple fibers", or "staple length fibers", as used herein, refer to fibers that are between about 0.125 inches and about 3.0 inches (about 3 millimeters and about 7.5 centimeters) in length.

The acquisition/distribution layers 46 can also contain absorbent gelling materials (also known as "hydrogels", "superabsorbent polymeric materials", or "supersorbers") provided that such materials are not present in such amounts or distributed in such a manner that they interfere with the desired acquisition and distribution characteristics of the acquisition/distribution layers 46. Absorbent gelling materials are described in greater detail in a number of references, including U.S. Pat. No. 4,781,711, issued to Dawn I. Houghton and Nicholas A. Ahr on Nov. 1, 1988, the disclosure of which is incorporated by reference herein. If the acquisition/distribution layers 46 contain absorbent gelling materials, the specific type of absorbent gelling materials used in the acquisition/distribution layers 46 can be different from the type(s) of absorbent gelling materials used in other parts of the absorbent core 42. Alternatively, the acquisition/distribution layers 46 can be substantially free of absorbent gelling materials.

Preferably, the acquisition/distribution layers 46 are comprised of at least some synthetic fibers (e.g., at least 10% by weight) so the acquisition/distribution layers 46 will be resilient enough to transport exudates throughout the core 42 when the absorbent article 20 is subjected to compressive forces when it is worn. Although natural fibers and absorbent gelling materials will provide the acquisition/distribution layers 46 with absorptive capacity and the ability to wick exudates, these characteristics are not absolutely required in the acquisition/distribution layers 46 of the present invention. Preferably, the acquisition/distribution layers 46 are comprised of nonwoven webs of synthetic fibers such as polyester, polyethylene, polyethylene terephthalate, and polypropylene fibers, and are substantially free of absorbent gelling materials. In one preferred embodiment, the acquisition/distribution layers 46 are nonwoven webs comprised of about 80% 15 denier per fiber polyester fibers, and about 20% binder fibers. (Denier is a unit of fineness for a fiber. A "denier" represents the fineness of a fiber weighing one gram for each 9,000 meters.)

There are a number of manufacturing techniques which may be used to manufacture the acquisition/distribution layers 46. For example, the acquisition/distribution layers 46 may be woven or nonwoven, e.g., air laid, spunbonded, carded or the like. A preferred material for the acquisition/distribution layers 46 is a carded and thermally bonded, low density nonwoven material. The fibers in the acquisition/distribution layers 46 may be bonded with a binder material such as acrylic latex rather than thermally bonded, or the fibers may be unbonded. In especially preferred embodiments, the fibers in the acquisition/distribution layers 46 are unbonded. In any event, the mater i al comprising the acquisition/distribution layers 46 should be arranged in an open structure to provide the desired void space.

Preferably, the acquisition/distribution layers 46 have a basis weight from about 0.5 to about 8 ounces per square yard (about 17 to about 270 grams per square meter), and a density from about 0.02 to about 0.10 grams per cubic centimeter (g/cc). The density of the acquisition/distribution layers 46 (and the storage layers 48, and any other layers for which densities are given) is calculated from the basis weight of the layer and its caliper. All measurements are made on newly unpacked, unfolded, and dissected absorbent articles. Unless otherwise stated, the densities and calipers are measured with a sample under a load of 0.1 psi (7 grams per square centimeter). The basis weight is measured by die-cutting a certain size sample and weighing the sample on a standard scale. The weight and area of the sample determine the basis weight of the sample. The caliper is measured using a standard gauge. The density and basis weight values of the acquisition/distribution layers 46 do not include the weight of any absorbent gelling materials contained in the layers. The density and basis weight values given below of the storage layers 48, however, include the weight of the absorbent gelling materials contained therein.

It should be understood that the characteristics (for example, the material composition, basis weight, and density) of the acquisition/distribution layers 46 may differ between layers when there are more than one acquisition/distribution layer 46.

For instance, in the case of the preferred embodiment shown in FIGS. 1-3, when there are two acquisition/distribution layers 46, the top acquisition/distribution layer, first acquisition/distribution layer 46', has a lower basis weight than the bottom acquisition/distribution layer, second acquisition/distribution layer 46". In the preferred embodiment shown in FIGS. 1-3, the first acquisition/distribution layer 46' has a basis weight that is preferably between about 0.5 and about 4 ounces per square yard (about 17 to about 135 grams per square meter), most preferably about 2 ounces per square yard (about 70 grams per square meter), and a density from about 0.03 to about 0.05 grams per cubic centimeter (g/cc). In this preferred embodiment, the lower acquisition/distribution layer, second acquisition/distribution layer 46", has a basis weight that is preferably between about 4 to about 8 ounces per square yard (about 70 to about 270 grams per square meter), most preferably about 6 ounces per square yard (about 200 grams per square meter), and a density from about 0.03 to about 0.05 grams per cubic centimeter (g/cc). As will be described in greater detail below, the corresponding storage layers 48 also preferably have upper layers with lower basis weights than those of the lower layers.

It is believed that such an arrangement (making the top layers thinner) will be more comfortable for the wearer. This is particularly true when the uppermost storage layer, such as first storage layer 48', has a large aperture 52 for allowing fluids to pass to the underlying layers. If the uppermost storage layer 48' has a large aperture, the wearer may notice the difference in thickness between the apertured portion of the uppermost storage layer and the unapertured portion of the uppermost storage layer. For this reason, it is desirable to make the uppermost storage layer relatively thin so the difference in thickness between the apertured and unapertured portions will be less noticeable. The uppermost acquisition/distribution layer 46' that forms the first pair of layers with the first storage layer 48', is also made relatively thin so that its size corresponds with the size of the first storage layer 48'.

The ability of the acquisition/distribution layers 46 to acquire and distribute exudates is referred to herein as the "horizontal fluid acquisition/distribution rate". The horizontal fluid acquisition/distribution rate may also be referred to by any abbreviated form of its name. The term "horizontal fluid acquisition rate", as used herein, refers to the rate at which the acquisition/distribution layers 46 allow fluid applied from a point source to enter and flow through itself while the layer is under a preselected pressure. The horizontal fluid acquisition rate is measured by the Horizontal Fluid Acquisition/Distribution Test described in Section 5. The term "point source" as used herein refers to the type of source of fluid that is described in Section 5. The point source is not, however, limited to single drops of fluid or the like.

The desired horizontal fluid acquisition rate of the acquisition/distribution layers 46 varies depending on the intended use of the absorbent article because the amount of fluids the absorbent article is required to handle will vary with the intended use of the absorbent article. The incontinent pad 20 illustrated in FIGS. 1-3 is intended for use by adults suffering from moderate to severe bladder incontinence. In this case, the horizontal fluid acquisition rate of the acquisition/distribution layers 46 should be at least about 8.0 cubic centimeters of synthetic urine/second (cc/sec) when the acquisition/distribution layer 46 being tested is under a pressure of about 0.4 pounds/square inch (psi.) (a pressure of about 28 grams per square centimeter). Preferably, the horizontal fluid acquisition rate of the acquisition/distribution layers 46 is at least about 12 cc/sec. under a pressure of about 0.4 psi (28 g/cm$^2$). In alternative uses, however, the horizontal fluid acquisition/distribution rate can be as low as about 2 cc/sec. of synthetic urine under a pressure of about about 28 g/cm$^2$. A horizontal fluid acquisition/distribution rate of about 2 cc/sec. would, for example, be suitable for use in a sanitary napkin, and a horizontal fluid acquisition/distribution rate of about 4 cc/sec. would be suitable for use in a disposable diaper. The acquisition/distribution layers 46 should, preferably, maintain the desired horizontal fluid acquisition/distribution rates after they have been wetted with exudates.

Preferably, the acquisition/distribution layers 46 are sufficiently wet resilient that they have a transverse post-compression recovery when wet of at least about 80% following compression of up to 25% of their width. To determine the transverse post-compression recovery, a sample of the acquisition/distribution layer material of a determined width is immersed in synthetic urine until substantially saturated. The saturated sample is placed on a platen or base plate between vise-like jaws. The jaws are brought together to reduce the width of the sample by about 75% and are held in the narrowing position for 30 seconds. The jaws are then released and the sample is allowed to recover for 30 seconds and the degree of recovery of the initial width is measured. The recovered width expressed as a percentage of the initial width is the transverse post-compression recovery.

The other type of layers that comprise the absorbent core 42 are the storage layers 48. The storage layers 48 serve to store exudates that have been transported to them for storage by the acquisition/distribution layer that lies above (and by the acquisition/distribution layer that lies below, if such a layer is present) each storage layer 48.

The storage layers 48 need not be especially effective for distributing exudates to other parts of the core 42. This requirement is preferably fulfilled by the acquisition/distribution layers 46. (The storage layers 48, should, however, allow exudates to move around within the storage layers themselves to the extent necessary to properly utilize the capacity of the storage layer.) The storage layers 48 can, therefore, be designed and constructed without being unduly burdened by considerations of exudate distribution. Such considerations would normally limit the storage capacity of the core by limiting the concentration and absorption speed of the absorbent gelling materials contained in the absorbent core.

Preferably, the storage layers 48 are capable of storing exudates as quickly as they are transported to the storage layers 48, or more quickly. The absorbent core 42 is preferably of such a construction that exudates will always have a place within the core 42 where they can be quickly stored until the capacity of the absorbent core 42 is reached. Such absorbent cores should not be subject to the prior problems, such as that of gel blocking, that caused the cores of many prior absorbent articles to be prematurely exhausted before their full capacity was used.

The storage layers 48 of the present invention are comprised at least partially of high-speed absorbent gelling materials. (That is, the storage layers 48 can be comprised partially of high-speed absorbent gelling materials, or entirely of such materials.) The term "absorbent gelling materials" as used herein generally refers to water-insoluble, water-swellable polymeric substances that are capable of absorbing water in an amount which is at least 10 times the weight of the substance in its dry form.

The term "high-speed"0 absorbent gelling materials as used herein, means those absorbent gelling materials that are capable of absorbing exudates at such a rate that they reach at least about 40%, preferably at least about 50%, and most preferably at least about 90% of their capacity in less than or equal to about 10 seconds. The percent rate of capacity can be measured using the "Tea Bag" Test described in Section 5.

Another way to express the rate at which absorbent gelling materials absorb fluids is by specifying the rate at which fluids are absorbed per weight of the absorbent gelling material (for example, the rate of absorption in grams per second per gram of absorbent gelling material). Expressed in this alternative manner, the preferred high-speed absorbent gelling materials referred to herein are those absorbent gelling materials that have a total capacity of at least about 25 times their weight in fluids, and are capable of absorbing fluids at the rate of at least about 0.8 grams/second per gram of absorbent gelling material (corresponds to the rate of about 40% capacity specified above), more preferably about 1.25 grams/second per gram of absorbent gelling material (corresponds to the rate of about 50% capacity), still more preferably 1.5 grams/second per gram of absorbent gelling material, and most preferably about 2.25 grams/second per gram of absorbent gelling material (corresponds to the rate of about 90% capacity). (All references herein to the number of times its weight that the absorbent gelling materials can absorb refers to multiples of the weight of the absorbent gelling materials in their dry form.)

Suitable high-speed absorbent gelling materials are currently available in a number of different forms. One type of absorbent gelling materials is in particulate form. The term "particulate", as used herein can refer to particles in any form, such as in the form of pellets or flakes. An example of particulate absorbent gelling material (though not necessarily high-speed particulate absorbent gelling materials) are those made in accordance with U.S. Pat. No. 4,654,039 issued Mar. 31, 1987 to Brandt, et al. the disclosure of which is incorporated by reference herein. Several types of absorbent gelling materials are discussed in U.S. Pat. No. 4,781,711 to Houghton, et al., previously incorporated by reference herein. The preferred form of absorbent gelling materials for use in the present invention, however, is a fibrous high speed absorbent gelling material.

The term "fibrous absorbent gelling materials" as used herein, means those absorbent gelling materials that are in the form of fibers. Such fibers (though not necessarily high-speed fibrous absorbent gelling materials) are discussed more fully in U.S. Pat. No. 4,855,179, issued Aug. 8, 1989, to Bourland, et al., the disclosure of which is incorporated by reference herein. The term "fibrous absorbent gelling materials", as used herein, is intended to include absorbent gelling materials in the form of fibers that are comprised entirely of absorbent gelling material and bi-component fibers that are comprised at least partially of other materials which have their surfaces coated with absorbent gelling materials.

Fibrous absorbent gelling materials are preferred for several reasons. Fibrous absorbent gelling materials can be easily incorporated into the structure of a nonwoven material. Fibrous absorbent gelling materials remain in place better than absorbent gelling materials in some other forms when compressive forces and other forces act on the absorbent article. Further, fibrous absorbent gelling materials are generally softer and more flexible than particulate absorbent gelling materials. Fibrous absorbent gelling materials also may have less tendency to cause holes in the backsheet 36 when they are in their dry state than some particulate absorbent gelling materials. Fibrous absorbent gelling materials can be distributed within a layer of material so that the fibers are generally spaced away from adjacent fibers a sufficient distance. As a result of this last characteristic, fibrous absorbent gelling materials will have a reduced tendency to come in contact with each other and cause gel blocking when they absorb liquids and swell.

A suitable fibrous high speed absorbent gelling material is known as FIBERSORB SA7000 and is available from Arco Chemical Company of Newton Square, Pa. FIBERSORB SA7000 is capable of absorbing fluid at the rate of at least about 1.9 grams per second per gram of such a material. An especially preferred fibrous high-speed absorbent gelling material is known as FIBERSORB SA7200, and is also made by Arco Chemical Company, but is not commercially available. FIBERSORB SA7200 is capable of absorbing fluid at the rate of at least about 2 grams per second per gram of such material.

It is desirable to use high speed absorbent gelling materials because, due to their high speed, they can substantially contribute to the immediately available capacity of the absorbent core 42. The absorbent gelling materials typically used in prior absorbent articles required several seconds or minutes to reach a substantial level of absorptive capacity. They were, therefore, of little value during the initial application of exudates to the absorbent articles. They became of significant value primarily during subsequent application of exudates.

It may be desirable to mix other materials with the high-speed absorbent gelling materials in the storage layers 48. There may be several purposes for including such other materials in the storage layers 48. Other materials may be used to hold the particles or fibers of the absorbent gelling material in place. They may also be used to bind the absorbent gelling material, or other components of the storage layers 48 together. They may be used to maintain space between the individual particles or fibers of absorbent gelling material in order to insure that adequate space is available for the absorbent gelling material to swell to its full size when it reaches its absorptive capacity.

The other materials that may be included in the storage layers 48 may be any of the types of materials specified above for use in the acquisition/distribution layers 46, and possibly a binder of some type.

However, as described in greater detail below, the characteristics (such as material composition, density, basis weight, and horizontal fluid acquisition rate) of the storage layers 48 do not have to be the same as the acquisition/distribution layers 46. The relative proportions of the types of the materials, in particular the amount of synthetic fibers that may be used, however, should be less than is used in the acquisition/distribution layers 46 because it is desirable to have greater absorptive capacity in the storage layers 48. The specific amounts of materials used are described below.

Binders, such as binder fibers, are used to bind the fibers that comprise the storage layers 48 to each other and to bind such fibers to the high-speed absorbent gelling materials used in the storage layers 48. A suitable binder fiber, if one is used, should be capable of bonding to the types of fibers described herein as being suitable for use in the storage layers 48 at temperatures that are less than the melting temperature of such fibers. A preferred commercially available binder fiber is known as KODEL 410 and is manufactured by the Eastman Chemical Products, Inc. of Kingsport, Tenn.

The composition of the materials used to form the storage layers 48 can vary within certain limits. All percentages of material composition referred to in this description are by weight, unless otherwise specified. The percentage of each of the materials used must be such that the total of the percentages equals 100%. In addition, all percentages of composition (and horizontal fluid acquisition/distribution) specified in this description and the appended claims are meant to include absorbent articles that have the specified percentage measured in some portion of the layer in issue (e.g., in at least some section of the absorbent article), regardless of whether the entire layer has the percentage in issue.

The storage layers 48 can contain between about 10% or 20% to about 100% high speed absorbent gelling materials; as much as about 80% natural fibers, such as wood pulp; as much as about 80% synthetic fibers, such as polyester fibers; as much as about 80% cross-linked cellulose fibers; and as much as about 20% binder fibers. When the storage layers 48 are described as having "as much as" a specified percentage of a material, this means that the material may be used in the layer, but it does not have to be present in the layer. In other words, the layer could have none of the material (0%), or it could have the material present in an amount between some small percentage such as 0.1% and the specified percentage of the material (e.g., 30%). One particularly preferred storage layer 48 is a thermally bonded mixture that contains about 50% FIBERSORB SA7000 absorbent gelling material, about 30% wood pulp, and about 20% KODEL 410 binder fiber.

There are a number of manufacturing techniques that may be used to manufacture the storage layers 48. For example, the storage layers 48 can be air laid, or carded. A preferred storage layer 48 is an air laid mixture of high speed absorbent gelling materials and airfelt. Typically, an air laying process involves mixing the components in air, and condensing and rearranging the mixture on a forming screen. Any suitable conventional air laying process may be used.

The storage layers 48 should have a basis weight of from about 0.01 to about 0.8 grams per square inch (from about 20 to about 1200 grams per square meter), and a density of less than about 3 grams per cubic inch (about 0.183 grams per cubic centimeter (g/cc)). As in the case of the acquisition/distribution layers 46, the characteristics (for example, the material composition, basis weight, and density) of the storage layers 48 may differ between layers when there is more than one storage layer 48.

Preferably, in the case of the preferred embodiment shown in FIGS. 1-3, where there are two storage layers, the top storage layer, first storage layer 48' has a basis weight from about 0.01 to about 0.4 grams per square inch (about 20 to about 600 grams per square meter), most preferably about 0.2 grams per square inch (about 300 grams per square meter), and a density of less than about 2 grams per cubic inch (about 0.12 g/cc), most preferably about 1.5 grams per cubic inch (about 0.092 g/cc). The lower storage layer, second storage layer 48", has a basis weight from about 0.2 to about 0.8 grams per square inch (about 300 to about 1200 grams per square meter), most preferably about 0.4 grams per square inch (about 600 grams per square meter), and a density of less than about 2 grams per cubic inch (about 0.12 g/cc), most preferably about 1.5 grams per cubic inch (about 0.092 g/cc).

The different layers of the multiple layer absorbent core 42 may be bonded together by any suitable means such as spray gluing, or they may be unbonded.

When there is more than one pair of the layers described above (that is, when there is more than one acquisition/distribution layer and more than one storage layer), there should be some type of interconnection between each pair of layers because exudates will generally not be able to travel through a full storage layer (such as first storage layer 48' shown in FIG. 2) to underlying acquisition/distribution layers and storage layers because of the reduction in void space therein and swelling of the absorbent gelling materials. A completely full storage layer will tend to block the flow of exudates. Thus, the pairs of layers, particularly the acquisition/distribution layers 46 in each pair, should be in fluid communication with each other. The term "fluid communication" simply means that fluids should be able to pass between the layers or pairs of layers. This fluid communication between the layers may be provided by any suitable means. For instance, in the embodiment shown in FIGS. 1-3, there is at least one fluid passageway or path (or simply "passageway") 50 for exudates to travel through from the one layer, such as first acquisition/distribution layer 46', to the underlying layers, such as second acquisition/distribution layer 46".

The terms "passageway" or "path", as used herein, refer to a structure through which exudates may flow from one layer to another layer. The passageway 50 may be any suitable structure that will allow exudates to flow from an upper acquisition/distribution layer to a lower acquisition/distribution layer or storage layer. The term "passageway" is thus not limited to a structure of any particular shape. For instance, a suitable passageway could comprise one or more apertures, one or more pieces of fluid pervious material that connect two layers, or it could comprise portions of the layers themselves, or an arrangement of layers that interconnect or simply touch each other. In addition, or as an alternative to the above, the passageway could comprise a low density area, or any of the other types of structures described in U.S. patent application Ser. No. 07/198,032 filed May 24, 1988 in the name of George S. Raising, et al., the disclosure of which was previously incorporated by reference herein and in U.S. Pat. No. 4,880,419 issued Nov. 14, 1989 to Irving S. Ness, the disclosure of which is hereby also incorporated by reference herein.

If the passageway 50 comprises one or more apertures 52, there are several factors that should be considered. The apertures 52 should be properly positioned, and should be sufficient in size to transfer exudates from one layer to another. The apertures 52 should be located at places where exudates would otherwise accumulate when the upper storage layer or layers reach capacity. Typically, this place will be immediately below the region where exudates are deposited onto the incontinent pad 20 (referred to as the "area or zone of typical exudate deposition"). The apertures 52 in each storage layer 48 should, therefore, be located between the transverse centerline t and the front end edge 24a (that is, in the front half of the incontinent pad 20). The width of the apertures 52 should be such that the apertures 52 do not close up if the incontinent pad 20 is compressed in the transverse direction when worn, or when the absorbent gelling materials swell when wetted. The incontinent pad 20 may have any number of apertures 52, from one to virtually an infinite number of a plurality or multiplicity of apertures.

Figure 4:
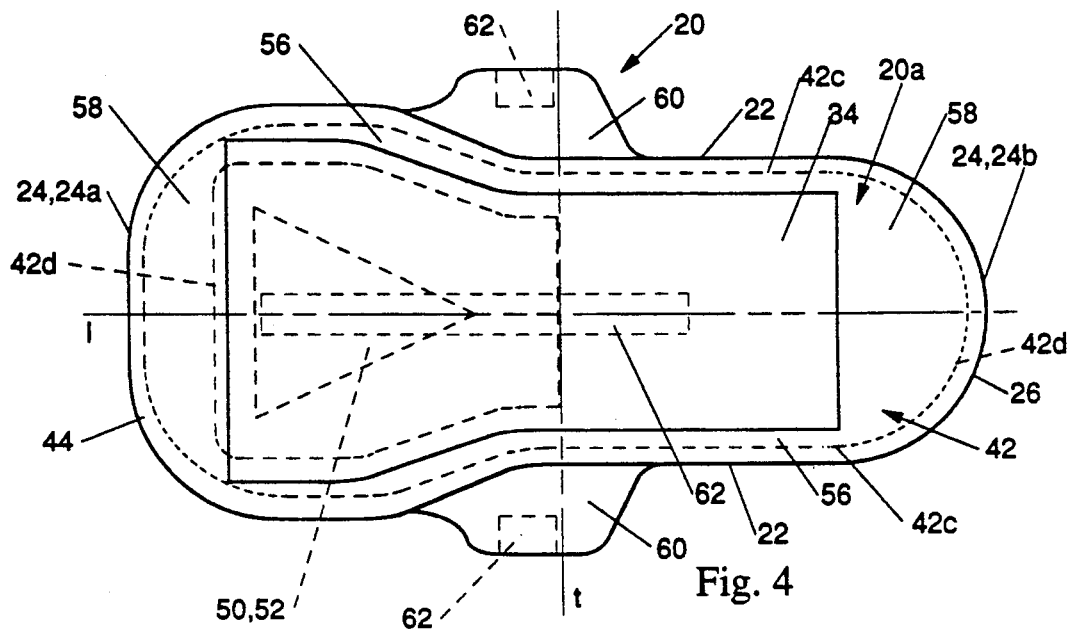
FIG. 4 is a plan view of an absorbent article having an aperture of a different configuration.

The area that the apertures 52 should be located in preferably, at a minimum, covers at least the area shown in dotted lines in FIG. 4. This area is in the shape of an isosceles triangle. The base of the isosceles triangle is generally perpendicular to the longitudinal centerline l, and is spaced about 2 inches (about 5 cm.) from the front end edge 24a of the incontinent pad 20. The length of the base of the triangular-shaped area is about 2 inches (about 5 cm.). The height is about 3 inches (about 7.6 cm.). The triangular-shaped area covers about 3 square inches (about 19 square centimeters).

A particularly preferred passageway 50 is shown in FIGS. 1-3. The passageway 50 shown in FIGS. 1-3 comprises a single aperture 52 in the first storage layer 48'. It is believed that when there is only one aperture 52 in the storage layer or layers 48, the dimensions of such a single aperture 52 need to be made relatively large to avoid the tendency of the aperture 52 to close up when the incontinent pad 20 is worn and shut off the flow of exudates to the lower layers. The aperture 52 extends the entire length of the first storage layer 48' in the embodiment shown in FIGS. 1-3. In the embodiment shown in FIGS. 1-3, the width of the aperture 52 is greater in the first end region 28 than in parts of the central region 30 and in the second end region 32 of the incontinent pad 20. Preferably, the width of the aperture 52 is at least about 2 inches (about 5 cm.) in the first end region 28. The preferred aperture 52 shown in FIGS. 1-3 has longitudinal side walls that follow the curvature of the longitudinal side edges 22 of the incontinent pad 20.

The storage layer 48' and the aperture 52 in the embodiment shown in FIGS. 1-3 can be thought of in an alternative manner since the aperture 52 is relatively wide and extends the full length of the core 42. The storage layer 48' can be thought of as being in the form of at least two strips of material, such as strips 48a' and 48b', instead of being in the form of a layer with an aperture. If the first storage layer 48' is thought of in this manner, in the preferred embodiment shown in FIGS. 1-3, the strips 48a' and 48b' that form the first storage layer 48' are preferably each between about 0.75 to about 1.5 inches (about 2 to about 4 cm.) wide.

FIG. 4 shows an alternative embodiment of the incontinent pad 20 of the present invention that has a single aperture 52 located in the area of typical liquid deposition, between the transverse centerline t and the front end edge 24a of the incontinent pad 20. As shown in FIG. 4, the edge of the aperture 52 closest to the front end edge 24a of the incontinent pad 20 may be spaced inward toward the transverse centerline t a distance of about 1 inch (about 2.54 cm.) since exudates are not usually deposited within the 1 inch region between the edge of the aperture 52 and the front end 24a of the pad 20.

Figure 5:
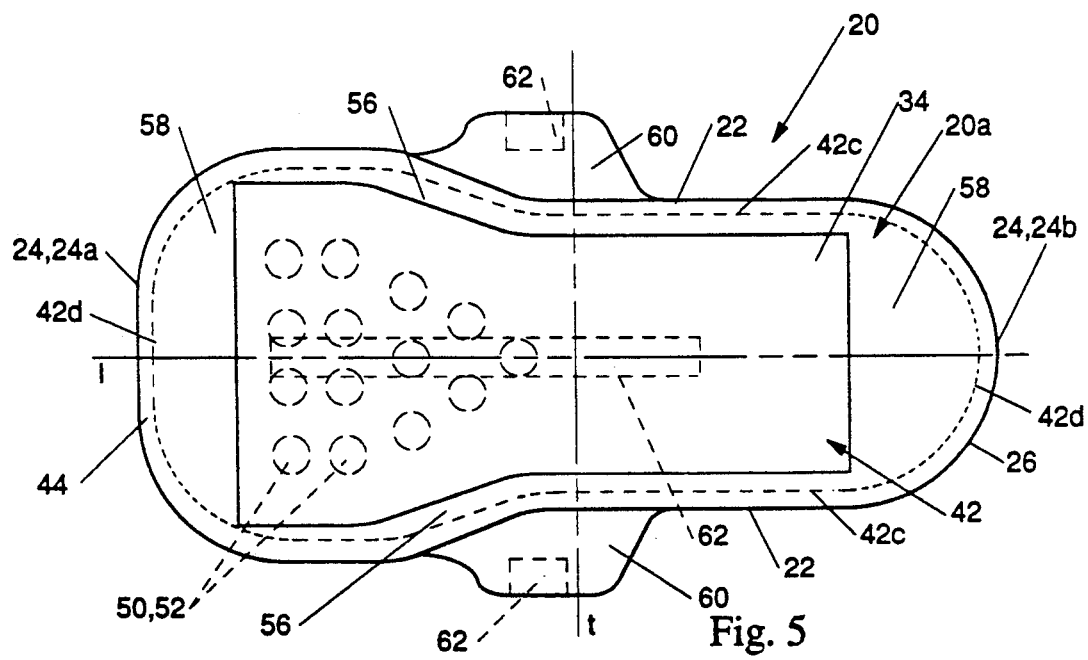
FIG. 5 is a plan view of an absorbent article having a multiplicity of apertures.

FIG. 5 shows an alternative embodiment of the incontinent pad 20 of the present invention that has a multiplicity of apertures 52. When there are a multiplicity of apertures 52 in the storage layer(s) 48, the size of each aperture 52 can be smaller than when there is only a single aperture 52. There will be less tendency for all of such apertures 52 to close up simultaneously. The apertures 52 should not be made so small, however, that absorbent gelling materials which have absorbed exudates and swelled block the openings that the apertures 52 provide. Preferably, each aperture 52 will have a width of at least about ¼ inch (about 0.65 cm.), although smaller widths are possible. The aperture or apertures 52 that connect the layers may be circular as shown in FIG. 5, or any other suitable shape, including square, rectangular, oval, and irregularly-shaped.

3. Optional Components of the Absorbent Article

The incontinent pad 20 of the present invention may be provided with optional additional components.

The incontinent pad 20 of the present invention may be provided with barrier shields along the edges of the pad. The incontinent pad 20 shown in FIG. 1 is provided with longitudinal barrier shields 56 along each longitudinal edge 22 of the pad and transverse barrier shields 58 along each transverse, or end edge 24 of the pad.

The longitudinal barrier shields 56 are used primarily for two purposes, although they may also serve other functions.

The longitudinal barrier shields 56 first serve to prevent those exudates that are in the process of being transported by the acquisition/distribution layers 46 from flowing out of the incontinent pad 20 along the longitudinal edges 22 of the same. As described above, the materials chosen for the acquisition/distribution layers 46 are typically very efficient at transporting liquid exudates in directions in the plane of the pad. This is particularly true when the acquisition/distribution layers 46 are made entirely of synthetic fibers since such fibers will not absorb fluids. In such embodiments, fluids will be transported so rapidly that they will literally flow out the sides of the core 42 if they are not restrained from doing so. The longitudinal barrier shields 56 prevent this from occurring.

Importantly, this first function of the longitudinal barrier shields 56 differs from the function of conventional barrier leg cuffs and the like. Conventional barrier leg cuffs serve primarily to contain exudates which have pooled on the surface of either the topsheet or absorbent core of the absorbent article from leaking out of the absorbent article. Thus, it is necessary that such conventional barrier leg cuffs form a "stand up" barrier to the flow of exudates. Ideally, there should be no pooling on top of the absorbent core of the present invention, so the longitudinal barrier shields 56 may lie flat on top of the topsheet 34. Alternatively, they may be positioned between the core 42 and the topsheet 34 and may lie flat on top of the core 42.

The second function of the longitudinal barrier shields 56 is to direct exudates toward portions of the core 42 that have capacity available to absorb exudates. Liquid exudates that are deposited on the core 42 will tend to be distributed by the acquisition/distribution layers 46 radially outward from the place where they were deposited. Since the core 42 of the incontinent pad 20 is made relatively narrow in comparison to its length, liquid exudates will reach the longitudinal edges 42c of the core 42 much sooner than they will reach the ends 42d of the absorbent core 42. The longitudinal barrier shields 56 direct exudates toward the ends 42d of the core 42, particularly toward the back end 42d' of the core 42. Since the back end edge 24b of the pad 20 is typically lower than the front end edge 24a when the incontinent pad 20 is worn, liquids will tend to flow by gravity towards the back end edge 24b along the longitudinal barrier shields 56.

The incontinent pad 20 may also be provided with one or more transverse barrier shields 58 along the end edges 24 of the pad. In the embodiment shown in FIG. 1, the incontinent pad 20 has a transverse barrier shield 58 along each end edge 24 of the pad. In alternative embodiments, however, the incontinent pad 20 of the present invention may only have one transverse barrier shield 58. In such a case, the transverse barrier shield 58 should preferably be positioned at the rear end edge 24b of the incontinent pad 20 because exudates will be more likely to leak out of the rear end edge 24b of the pad, rather than out of the front end edge 24a since (as described above) the front end edge 24a is likely to be more elevated when worn. Liquid exudates will generally not tend to flow out of the front end edge 24a of the pad 20 unless there are some wicking fibers in the core at this end of the pad.

The barrier shields may be manufactured from a wide variety of materials such as polyethylene, polypropylene, polyester, rayon, nylon, foams, plastic films, formed films, and elastic foams. A number of manufacturing techniques may be used to manufacture the barrier shields from these materials. For example, the barrier shields may be woven, nonwoven (e.g., spunbonded, carded, or the like). One particularly preferred barrier shield comprises a two layer laminate comprising a layer of nonwoven material and a polyethylene film. In other alternative embodiments, the barrier shields may comprise a material, such as a low tack or no tack hot melt material, that is printed on the incontinent pad 20. Such an alternative type of barrier shield may be printed by any suitable process, including by gravure printing or flexographic printing processes.

If desired, the incontinent pad 20 may be additionally provided with flaps 60 that extend outwardly from each longitudinal edge 22 of the incontinent pad 20. The flaps 60 may be in any suitable configuration. Suitable flaps 60 may, for example, be made in accordance with the teachings of U.S. Pat. No. 4,589,876, issued May 20, 1986 to Van Tilburg and U.S. Pat. No. 4,687,478, issued Aug. 18, 1987 to Van Tilburg, the disclosures of which patents are incorporated herein by reference.

In addition, as shown in FIG. 2, the garment side 36b of the backsheet 36 may include a means for attaching the incontinent pad 20 to the undergarment of the wearer ("attaching means") 62. Preferred attaching means 62 may include mechanical fasteners or, more preferably, adhesive fastening means, such as a pressure sensitive adhesive. The pressure sensitive adhesive may be applied to the garment side 36b of the backsheet 36 in a number of different configurations.

Such configurations include, but are not limited to a single strip of adhesive 62 along the longitudinal centerline l of the incontinent pad 20 (shown in FIG. 1), two parallel strips of adhesive, two symmetrically opposite, convex outwardly oriented strips of adhesive, a generally centered rectangular patch of adhesive, or patches of adhesive disposed near the distal end of each flap 60 (i.e., the end of the flaps 60 farthest away from the longitudinal centerline l of the incontinent pad 20). If the adhesive is provided in the form of strips, the strips of adhesive are preferably between about 10 to about 20 cm in length, and between about 5 to about 35 millimeters in width. If the adhesive is applied to the backsheet 36 in a generally centered rectangular patch (not shown), it should cover about 30 to about 70 percent of the area of the garment side 36b of the backsheet 36. Suitable adhesive may be that specified as 0.6 mil pass available from Century Adhesive as product number A305-4, or from Anchor Continental, Inc., 3 Sigma Division, of Covington, Ohio.

4. Alternative Embodiments of the Present Invention

There are many possible alternative embodiments of the absorbent article 20 of the present invention and of the multiple layer absorbent core 42 incorporated therein. These include, but are not limited to the embodiments described below.

In one alternative embodiment that can be discussed with reference to FIGS. 1-3, the topsheet 34 may be eliminated, and the uppermost acquisition/distribution layer 46' can serve the function the topsheet 34 generally serves. Another way of describing such an embodiment would be to say that the topsheet 34 and the uppermost acquisition/distribution layer 46' are one and the same. The acquisition/distribution layer material described herein is suitable for use as a topsheet because it drains rapidly, and thus provides a dry surface for contact with the wearer's skin.

In one version of this first alternative embodiment, the first acquisition/distribution layer 46' may be arranged in the form of one or more layers or strata, each of which is provided with its own particular characteristics. For instance, the uppermost layer of the first acquisition/distribution layer 46' could be comprised of a web of material (such as a nonwoven web of 3 denier fibers) that is soft and comfortable against the wearer's skin, and the remainder of the first acquisition/distribution layer 46' could be comprised of a nonwoven web of 15 denier fibers.

In this first alternative embodiment, the multiple layer absorbent core 42 of the present invention may be referred to as a multiple layer absorbent "body", rather than as a core since it will be positioned adjacent to and secured to the backsheet 36, and will no longer be positioned between two elements such as the topsheet 34 and the backsheet 36.

Figure 6:
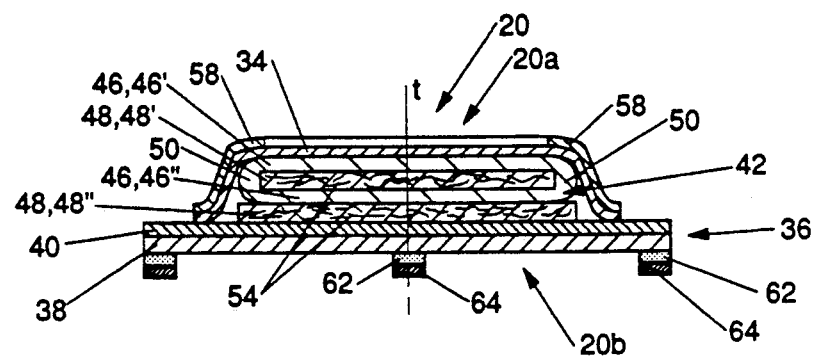
FIG. 6 is a transverse sectional view taken from an angle similar to that of FIG. 2 of an embodiment of the absorbent article of the present invention which has an alternative core arrangement.

FIG. 6 shows another possible alternative embodiment of the multiple layer absorbent core 42 of the present invention In the embodiment shown in FIG. 6, the mechanism used to transport exudates from the upper acquisition/distribution layer 46' of the core 42 to the lower acquisition/distribution layer 46" comprises portions of the acquisition/distribution layer material that interconnect (or join) the first acquisition/distribution layer 46' and the second acquisition/distribution layer 46'. The acquisition/distribution layer material that joins the first acquisition/distribution layer 46' to the second acquisition/distribution layer 46" can be pieces of material that are separate from the first and second acquisition/distribution layers 46' and 46". Alternatively, the material that joins the two acquisition/distribution layers could be part of one of the acquisition/distribution layers, or as shown in FIG. 6, part of both of the acquisition/distribution layers (in one version of the embodiment shown in FIG. 6, both acquisition/distribution layers are the same web of material). The portions of the acquisition/distribution material that join the first and second acquisition/distribution layers can join such layers along the entire perimeters of these layers, or any portion thereof, such as only along the longitudinal edges. The different ways of interconnecting the acquisition/distribution layers described herein can be used in addition to, or as an alternative to the apertures 52.

Figure 7:
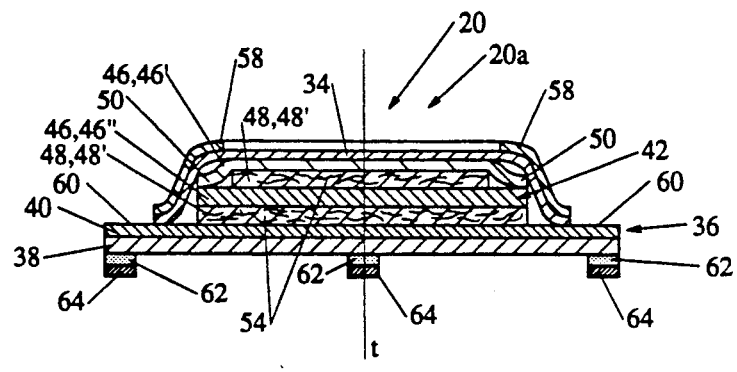
FIG. 7 is a transverse sectional view similar to that of FIG. 6 of an embodiment of the absorbent article of the present invention which has another alternative core arrangement.

FIG. 7 shows an alternative arrangement for allowing exudates to travel from the first acquisition/distribution layer 46' to the second acquisition/distribution layer 46". In the embodiment shown in FIG. 7, one or more of the acquisition/distribution layers 46 is simply made wider (or longer, or both) than the intermediate storage layer 48 so the acquisition/distribution layers 46 touch. In this alternative arrangement, it is not necessary that the acquisition/distribution layers 46 be joined to each other, as long as they are in contact.

Figure 8:
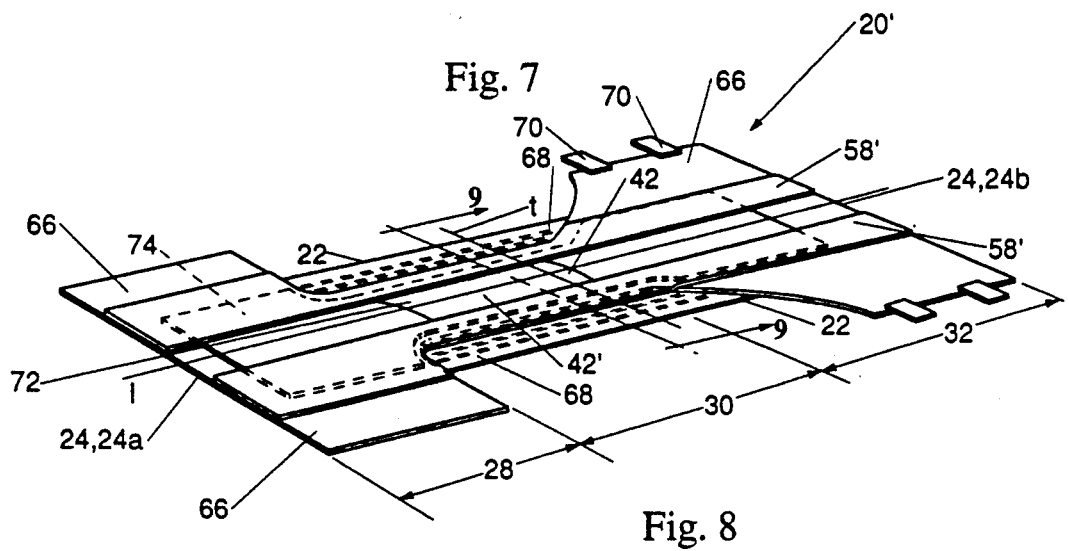
FIG. 8 is a perspective view of an incontinent brief that includes the absorbent core of the present invention.

FIG. 8 shows an alternative embodiment in which the multiple layer absorbent core 42 of the present invention is placed in a brief-type incontinent pad (or "brief") 20'. The brief-type incontinent pad 20' has the same general components described above (longitudinal and transverse centerlines l and t; first end region 28, central region 30, and second end region 32; topsheet 34, backsheet 36, and core 42', and the like). In addition, the brief 20' also has panels (or "ears") 66 in both the first and second end regions 28 and 32 adjacent the longitudinal edges 22 of the brief 20', and elastically contractible leg cuffs 68. The panels 66 are those portions of the brief 20' that overlap (at least partially) when the brief 20' is fastened about the waist of the wearer. The brief 20' also has a fastening system for forming a side closure. The fastening system can be any fastening system known in the art such as the tape tabs 70 shown in FIG. 8.

In this embodiment, the multiple layer absorbent core 42 of the present invention is a subcomponent of the absorbent core 42' of the brief 20'. The multiple layer absorbent core 42 of the present invention may be referred to as the "multiple layer absorbent body" in such a case to designate the fact that it is but one part of the absorbent core 42'. As shown in FIG. 8, the multiple layer absorbent body 42 is smaller in length and width than several other components of the absorbent core 42' of the brief 20'. The term "subcomponent", as used herein, means that the multiple layer absorbent body 42 is merely one component of the absorbent core 42', and that there are other absorbent components between the topsheet 34 and the backsheet 36. The multiple layer absorbent body 42 is generally rectangular in shape, and is positioned almost entirely in the central (or crotch) portion of the brief 20'.

Figure 9:
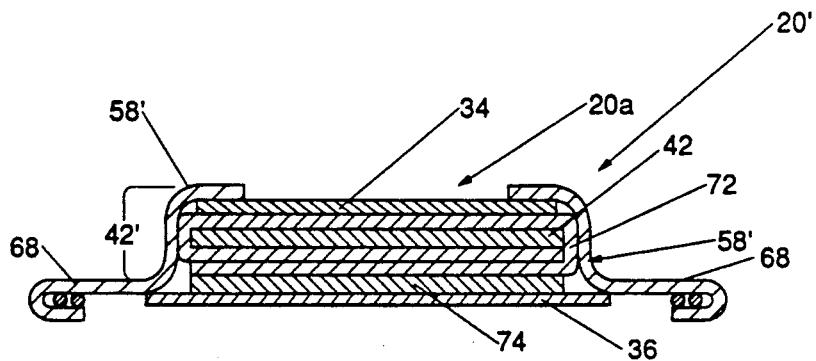
FIG. 9 is a transverse sectional view of the incontinent brief shown in FIG 8, taken along line 9—9 of FIG. 8.

The cross-section of the brief 20' is shown in FIG. 9. The multiple layer absorbent body 42 of the present invention is shown schematically in FIG. 9 for simplicity of illustration. It should be understood that the multiple layer absorbent body 42 in this embodiment can be any of the variations of the multiple layer absorbent core 42 disclosed in this description. As shown in cross-section, the multiple layer absorbent body 42 is wrapped in a low density (or "high loft") wrapping of material that is capable of transporting fluids ("fluid transporting wrapping" or "wrapping") 72. In one preferred embodiment, this high loft wrapping of material 72 has a caliper of about 65 mils (about 1.6 mm.) when measured in a flat, unwrapped condition under a pressure of about 0.1 psi (about 7 g/cm$^2$). The wrapped multiple layer absorbent body is positioned on top of (in other words, it overlies) a layer of storage layer material, such as a layer of airfelt 74. In the preferred embodiment, this layer of airfelt 74 has a basis weight from between about 0.1 to about 0.5 grams per square inch (about 160 to about 780 grams per square meter), most preferably about 0.2 grams/square inch (about 310 grams per square meter). The additional components of this embodiment (the wrapping of material 72 and the layer of airfelt 74) may be either secured to each other and/or secured to other components of the brief 20', such as the multiple layer absorbent body 42 and the topsheet 34 and backsheet 36, or they may be unsecured.

In this preferred embodiment, the layer of airfelt 74 serves as an additional storage layer. This layer of airfelt 74 is useful in incontinent brief-type products intended for use by severely incontinent persons, and is particularly suited for handling multiple loadings of exudates. The high loft wrapping of material 72 serves as an additional acquisition/distribution layer to transport exudates to the layer of airfelt 74. Thus, it could be comprised of any of the materials specified herein as being suitable for use in the acquisition/distribution layers 46. In other variations of the embodiment shown in FIG. 9, the wrapping could be eliminated, and liquid exudates could be transported to the layer of airfelt by apertures provided in the lowermost storage layer 48 of the multiple layer absorbent body 42, or by any of the other mechanisms described above as providing suitable passageways for the flow of exudates. In still other alternative arrangements, the layer of airfelt 74 may include any of the types of absorbent gelling materials disclosed herein, including ordinary speed absorbent gelling materials and/or high-speed absorbent gelling materials. (It should also be understood that the wrapping and the additional layer of storage layer material, could also be used in any other embodiments described herein.)

The brief 20' is provided with longitudinal barrier shields 58' along each longitudinal edge 22. The longitudinal barrier shields 58' need only extend along at least a portion of at least one longitudinal edge 22 of the brief 20'. In one preferred embodiment shown in FIG. 8, however, the longitudinal barrier shields 58' are essentially rectangular strips of material that run the length of the brief 20' and lie flat on top of the topsheet 34. As shown in FIG. 9, the topsheet 34 does not wrap around and cover the longitudinal sides of the absorbent core as it did in the incontinent pad shown in FIGS. 1-3. In the brief 20', this function is served by the longitudinal barrier shields 58'. In the preferred embodiment of the brief 20', the longitudinal barrier shields 58' are about 2.75 inches wide (about 7 cm.), and of this width of material, about 0.75 inches (about 2 cm.) lies directly above the absorbent core 42'. The remainder is wrapped around the sides of the absorbent core 42' and secured to the backsheet 36. The inside edges of the longitudinal barrier shields 58' (that is, the longitudinal edges of the barrier shields 58' located closest to the longitudinal centerline) are preferably spaced about 2.5 inches (about 6.4 cm.) apart.

The longitudinal barrier shields 58' may be made of any of the materials specified above as being suitable for the barrier shields of the incontinent pad 20 shown in FIGS. 1-3. Preferably, the longitudinal barrier shields 58' comprise a two layer laminate comprising a layer of nonwoven material and a polyethylene film. The longitudinal barrier shields 58' are oriented so the nonwoven material side faces upward in order than the brief 20' will be more comfortable to wear.

In still other alternative embodiments, the multiple layer absorbent core 42 of the present invention could, for example, instead of being incorporated into the incontinent pads 20 shown in the drawings, be incorporated into other types of absorbent articles, such as the disposable diapers described in U.S. Pat. No. 26,151 entitled "Disposable Diaper" which reissued to Robert C. Duncan and Norma L. Baker on Jan. 31, 1967; in U.S. Pat. No. 3,860,003 entitled "Contractable Side Portions For Disposable Diaper" which issued to Kenneth B. Buell on Jan. 14, 1975; and in U.S. Pat. No. 4,834,735 entitled "High Density Absorbent Members Having Lower Density And Lower Basis Weight Acquisition Zones" which issued to Miguel Alemany and Charles J. Berg on May 30, 1989, the disclosures of which are incorporated herein. Such different types of absorbent articles will, of course, have their own optional components such as elasticized barrier cuffs 68 which are discussed more fully in the above references, the disclosures of which are incorporated fully herein.

5. Test Methods

Horizontal Fluid Acquisition/Distribution Rate Test

The rate at which the material used in the acquisition/distribution layers 46 can acquire and distribute fluids is measured by a test which has been developed for this particular purpose. This test is known as the "Horizontal Fluid Acquisition/Distribution Rate Test" because rate of flow through the sample is measured while the sample is in a horizontal position during the test. The test described herein may be referred to by any abbreviated version of its name, such as the "Fluid Acquisition/Distribution Rate Test".

In the Fluid Acquisition/Distribution Rate Test, fluids are applied to a sample at a predetermined rate. The rate at which fluids are applied may exceed the rate at which the sample can acquire and distribute these fluids, and fluids may back up and pool on top of the sample. The rate at which fluids that cannot be acquired and distributed by the sample (the overflow rate) is measured. The difference between the rate at which fluids are applied to the sample and the overflow rate determines the rate at which the sample can acquire and distribute fluids.

Figure 10:
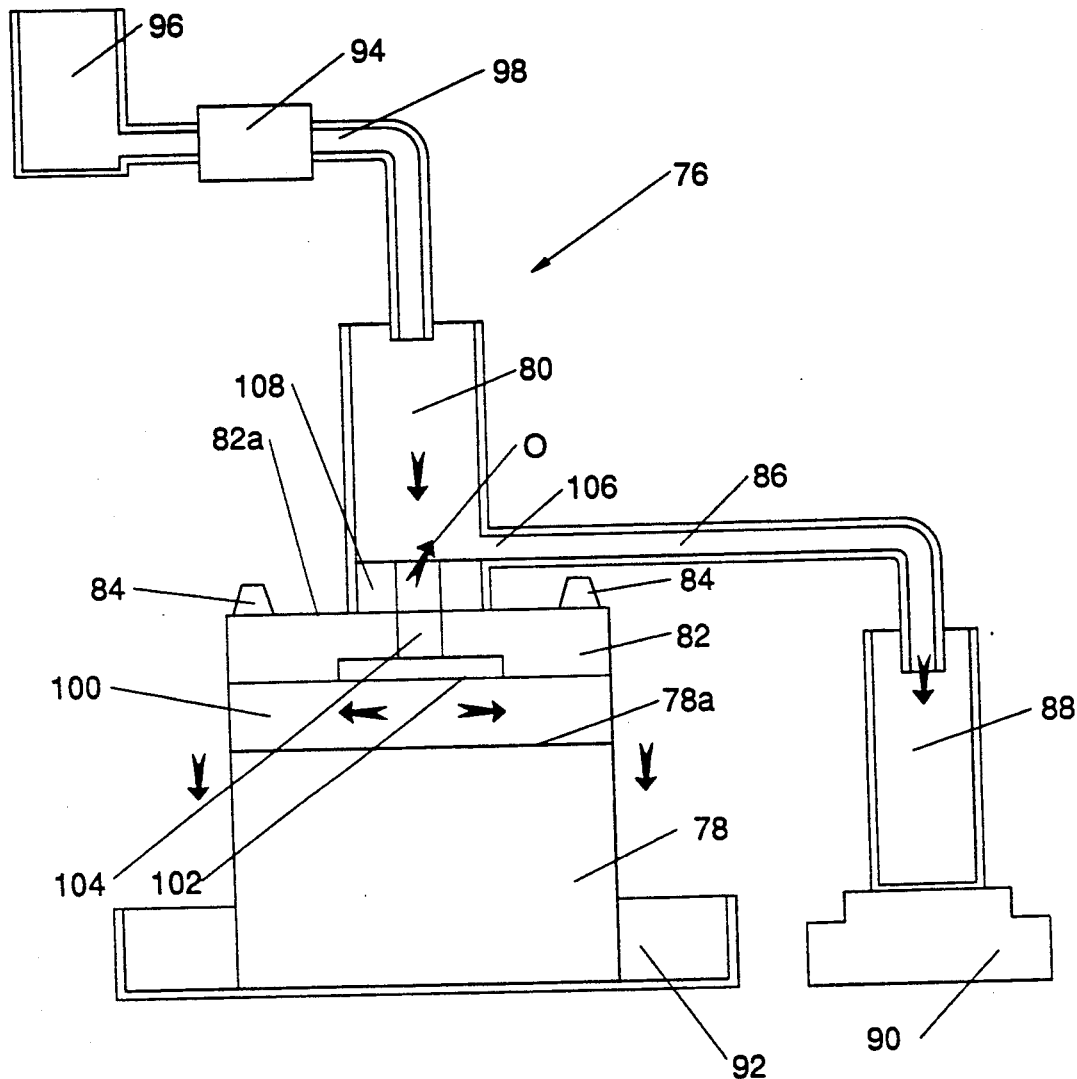
FIG. 10 is a schematic view of the apparatus used in the Horizontal Fluid Acquisition/Distribution Rate Test.

The Fluid Acquisition/Distribution Rate Test utilizes a device 76 which is depicted schematically in FIG. 10. FIG. 10 is a side view of the Fluid Acquisition Rate Test device 76. As shown in FIG. 10, the Fluid Acquisition Rate Test device 76 has as its basic components, a sample platform 78; a fluid holding column 80; a column base 82 provided with removable weights 84; a fluid overflow tube 86; a fluid overflow catch basin 88; a balance 90; a fluid catch basin 92; an adjustable flow rate pump ("pump") 94; a fluid reservoir 96; a fluid delivery tube 98, and a plug 108.

The sample platform 78 is a Plexiglas cube measuring 4 inches×4 inches×4 inches (10.2 cm.×10.2 cm.×10.2 cm.) which has a top surface designated 78a. The sample platform 78 provides a surface against which pressure can be exerted on the sample 100.

The fluid holding column 80 is constructed of Plexiglas tubing. It has a circular cross-section with an inside diameter of 1.5 inches (3.8 cm.) and an outside diameter of 1.75 inches (4.44 cm.). The length of the fluid holding column 80 should be in the range of between 7 inches and 9 inches (between 17.8 cm. and 22.9 cm.). One end of the fluid holding column 80 is permanently affixed to the center of the top surface 82a of the base 82 so that the fluid holding column 80 is perpendicular to the base 82.

The fluid holding column base, base 82, is constructed of a square piece of Plexiglas 4 inches×4 inches (10.2 cm.×10.2 cm.) and 0.5 inch (1.3 cm.) thick. The base 82 has a top surface 82a and a bottom surface 82b. A two inch (5.08 cm.) circular first hole 102 is drilled partially through the thickness of the base 82 from the bottom surface 82b of the base 82. The center of the first hole 102 is located in the center of the bottom surface 82b of the base 82. The first hole 102 penetrates the bottom surface 82b of the base 82 a depth of 0.0625 inches (0.159 cm.). A second circular hole 104 is drilled completely through the thickness of the base 82 in center of the base 82. The second hole 104 has a diameter of 0.5 inches (1.27 cm.).

The fluid overflow tube 86 is affixed to the fluid holding column 80. The fluid overflow tube 86 is constructed of Plexiglas tubing. The fluid overflow tube 86 has a circular cross-section with an inside diameter of 0.5 inches (1.27 cm.) and an outside diameter of 0.625 inches (1.59 cm.). A 0.625 inch (1.59 cm.) diameter circular hole, third hole 106, is drilled in the fluid holding column 80 to accommodate the attachment of the fluid overflow tube 86. This third hole 106 is drilled perpendicular to the length of the fluid holding column 80 and is located such that its center is 1.25 inches (3.18 cm.) above the bottom surface 82b of the base 82. One end of the fluid overflow tube 86 is inserted into this third hole 106 in the fluid holding column 80 and the fluid overflow tube 86 is affixed to the fluid holding column 80. The end of the fluid overflow tube 86 should not penetrate into the fluid holding column 80 beyond the interior wall of the fluid holding column 80. The fluid overflow tube 86 should be supported entirely by the fluid holding tube 80. The fluid overflow tube 86 should be positioned so that fluids which back up on the sample 100 and enter the fluid overflow tube 86 will flow by gravity out the unattached end of the fluid overflow tube 86 into the fluid overflow catch basin 88.

The plug 108 occupies the space inside the fluid holding column 80 between the top surface 82a of the base 82 and the hole 106 that forms the opening for the fluid overflow tube 86. The plug 108 is a cylindrical Plexiglas tube with an outside diameter of 1.5 inches (3.8 cm.) and an inside diameter of 0.5 inches (1.3 cm.). The plug 108 has a length of 0.5 inches (1.3 cm.). The plug 108 is inserted into the fluid holding column 80 so that is rests on the top surface 82a of the base 82.

The fluid overflow catch basin 88 can be any suitable vessel that is capable of catching and holding the fluid, represented by the arrow "O", that flows out of the unattached end of the fluid overflow tube 86.

The balance 90 can be any suitable balance that is capable of measuring the weight of the overflow catch basin 88 plus any fluid it may contain.

The fluid catch basin 92 can be any vessel capable of catching and holding any fluids which run out of the sample 100. The fluid catch basin 92 must be of such size that the fluids collected therein do not reach the height of the bottom of the sample 100.

The pump 94 can be any variable speed pump that is capable of delivering fluid through the delivery tube 98 at a rate of 15 cubic centimeters±0.15 cubic centimeters/second. The fluid reservoir 96 can be any suitable vessel that is capable of holding all the fluid needed for the test.

The fluid delivery tube 98 can be any conduit that is compatible with the pump 94 and the fluid reservoir 96. The fluid delivery tube 98 is positioned so that fluids are discharged into the open top of the fluid holding column 80.

The test is performed by first cutting a 4 inch by 4 inch square (10.2 cm. by 10.2 cm.) sample 100 of the material to be tested. The sample 100 is placed on the top surface 78a of the sample platform 78. The top surface 78a of the sample platform 78 must be horizontal. The edges of the sample 100 are aligned even with the edges of the sample platform 78. The fluid holding column base 82 is placed on top of the sample 100 so that the bottom surface 82b of the base 82 is in contact with the sample 100. The edges of the base 82 are aligned even with the edges of the sample 100. The weights 84 are equally distributed near the perimeter of the base 82 so they exert equal pressure on all portions of the sample 100. The amount of weight used should be such that the total weight of the weights 84, the fluid holding column base 82, the fluid holding column 80, and the fluid overflow tube 86 equals 2900 grams.

The pump 94 is set to deliver a fluid at a rate of 15 cubic centimeters/second for a period of ten seconds. The fluid used is a synthetic urine known as Jayco SynUrine which is available from Jayco Pharmaceuticals Company of Camp Hill, Pa. The formula for the synthetic urine is: 2.0 g/l of $KCl$; 2.0 g/l of $Na_2SO_4$; 0.85 g/l of $(NH_4)H_2PO_4$; 0.15 g/l $(NH_4)H_2PO_4$; 0.19 g/l of $CaCl_2$ and 0.23 g/l of $MgCl_2$. All of the chemicals are of reagent grade. The pH of the synthetic urine is in the range of 6.0 to 6.4.

The pump 94 is started and synthetic urine is delivered to the sample at the rate of 15 cubic centimeters/second for a period of 10 seconds±0.1 seconds. The synthetic urine is pumped from the fluid reservoir 96 by the pump 94 through the fluid delivery tube 98 into the fluid holding column 80. The synthetic urine is applied to the sample 100 through the hole in the base 82 of the fluid holding column 80. The synthetic urine typically flows through the sample 100 in the direction of the arrows, and then flows out of the sample 100 where it is collected in the fluid catch basin 92.

If the rate at which the fluid can flow into and through the sample 100 is less than the rate at which fluid is being pumped, fluid backs up in the fluid holding column 80. When the level of fluid held in the fluid holding column 80 reaches the level of the fluid overflow tube 86, the fluid begins to flow through the fluid overflow tube 86 and is collected in the fluid overflow catch basin 88. The weight of fluid present in the fluid overflow catch basin 88 is measured by the balance 90.

The pump 94 is stopped after 10 seconds±0.1 seconds. The weight of fluid in the overflow catch basin 88 is then recorded.

The Fluid Acquisition/Distribution Rate described herein is the average flow rate of synthetic urine in cubic centimeters through the sample over the ten second test period. It is calculated as follows:

$$\text{Fluid Acquisition/Distribution Rate (cc/sec.)} = \frac{155 \text{ cc} - W}{10 \text{ sec.}}$$

Where W = weight of fluid in the fluid overflow collection basin after 10 seconds (in cubic centimeters)

Absorption Rate/Capacity Test ("Tea Bag" Test)

The rate at which the absorbent gelling material absorbs fluids and the absorptive capacity of the absorbent gelling materials used in the storage layers 48 is measured by a test that will be referred to as the "Absorption Rate/Capacity Test" or the "Tea Bag" Test. The Tea Bag Test is a type of test that is fairly standard in the industry among those who use absorbent gelling materials. It is important, however, that the specific version of the Tea Bag Test described herein be followed.

The test essentially involves placing the absorbent gelling material to be tested within a "tea bag" and dipping the tea bag into a synthetic urine solution for a specified period of time. For the purposes of this test, the Absorptive Capacity of the absorbent gelling material is the amount of synthetic urine the absorbent gelling material absorbs over a ten minute time period. The Absorptive Capacity is generally expressed in units of grams of fluid absorbed per gram of absorbent gelling material. The percent of absorptive capacity the absorbent gelling material is capable of absorbing in ten seconds is equal to the ratio of the absorptive capacity after ten seconds to the Absorptive Capacity (after ten minutes) multiplied by 100.

| Apparatus | |
|---|---|
| The following equipment is needed for the Tea Bag Test: | |
| Balance | Top loading, 1 mg sensitivity, Mettler PC-220, Fisher #01-913-382, or equivalent |
| Beaker | 2,000 ml., Kimax brand, Fisher #02-539R, (and other sizes as needed), or equivalent |
| Heat Sealer | T-Bar plastic Model T-7, 115V, 65W, Harwil Co., Santa Monica, California, or equivalent |
| Paper | Tea bag, Dexter 1234-heat sealable, or lower porosity, if required, Dexter Corp., Windsor Locks, CT 06096, or equivalent |
| Timer | A timer able to time 10 minutes ± 0.1 seconds, Fisher #14-653, or equivalent |
| Paper | Weighing, Fisher #09-898-12A, or equivalent |
| Scissors | Standard type |
| Tongs | Crucible, Fisher #15-200, or equivalent |
| Ruler | Stainless steel metric, from L. S. Starrett, Athol, Mass. 01331, or equivalent |
| Solutions | |
| The following solution is needed: | |
| Synthetic Urine | Jayco SynUrine from Jayco Pharmaceuticals Company of Camp Hill, Pennsylvania, or equivalent |

Procedure

The following procedure is conducted under standard laboratory conditions at 23° C. (73° F.) and 50% relative humidity.

The tea bag material is cut into 6 cm × 12 cm rectangles, using scissors or a 6 cm × 12 cm cutting die. The cut tea bag material is then folded in half lengthwise and sealed along any two open sides with a T-bar sealer to produce 6 cm × 6 cm tea bag squares.

After the tea bag has been prepared, 0.200 grams, plus or minus 0.005 grams, of the absorbent gelling material is weighed on weighing paper. The absorbent gelling material is then transferred into a tea bag. The top (or open end) of the tea bag is sealed. An empty tea bag is sealed at the top and is used as a blank.

Approximately 400 milliliters of saline solution is poured into the 2,000 milliliter beaker. The blank tea bag is submerged in the saline solution. The tea bag containing the absorbent gelling material (the sample tea bag) is held horizontally to distribute the material evenly throughout the tea bag. The tea bag is laid on the surface of the saline solution. The tea bag is submerged in the synthetic urine and soaked for 10 seconds±0.1 seconds.

After soaking both tea bags in the saline solution for a period of 10 seconds±0.1 seconds, the tea bags are removed. The tea bags are removed using the tongs to grip the edges of the tea bags. The edges of the tea bags are gripped so that the folded edge of each bag is down. The tea bags are suspended with the folded edge down. The tea bags should not touch each other or the work area. One method for hanging the tea bags is to set up a rod with clamps between two stands. Binder clips may be attached to the rod and the tea bags may be suspended from the binder clips.

After a drying period of 10 minutes±10 seconds, both the sample and the blank tea bags are weighed. The weight of the sample tea bag is recorded as $W_1$, and the weight of the blank tea bag is recorded as $W_2$.

The above procedure is repeated with another sample and blank tea bag and the soak time is changed to 10 minutes±10 seconds to approximate the total absorptive capacity of the absorbent gelling material. The weight of the sample tea bag is recorded as $W_{10}$, and the weight of the blank tea bag is recorded as $W_{20}$.

The percentage of absorptive capacity for a period of ten seconds for the sample is calculated as follows:

$$\text{Absorptive capacity after ten seconds, } A_1 \text{ (g/g)} = \frac{(W_1 - W_2)}{0.20 \text{ g}}$$

(Where 0.20 grams is the dry weight of the sample)

$$\text{Absorptive capacity after ten minutes, } A_2 \text{ (g/g)} = \frac{(W_{10} - W_{20})}{0.20 \text{ g}}$$

$$\text{Percentage of Capacity Used in 10 Seconds} = \frac{A_1}{A_2} \times 100$$

The average rate of fluid absorbency in grams of synthetic urine per second per gram of absorbent gelling material can also be calculated using the Tea Bag Test. The following calculation is used:

$$\text{Average Rate of Fluid Absorbency Over 10 Second Period (g/g/sec.)} = \frac{A_1 \text{ g/g}}{10 \text{ sec.}}$$

(Where 10 seconds is the length of time the sample was submerged

-continued
in the synthetic urine.)

In use, it is believed that the exudate acquisition/distribution layer is capable of quickly absorbing exudates as they are deposited on the absorbent article and distributing such exudates to the lower storage layer in a manner that substantially reduces or eliminates prior problems of saturation of the materials adjacent the zone of exudate application and gel blocking. It is believed that the combination of the layers of the particular materials used provides a structure that is also capable of quickly storing the absorbed liquids.

While not wishing to be bound by any particular theory, it is believed that the multiple layer absorbent core distributes exudates by a cascading effect. It is believed that the manner of acquisition, distribution, and storage of the multiple layer absorbent core can be analogized to the filling of an ice cube tray with water in that when one region of the absorbent core is filled, exudates will quickly flow laterally to the sides of the filled region to begin filling other unfilled regions.

The present invention, in theory, operates by a using a layer that has good fluid transporting properties in the X-Y plane as the top layer (referred to herein as "horizontal" fluid acquisition/distribution), and provides a storage layer underneath the top layer. The storage layer need not be particularly good at transporting fluids in the X-Y plane. In fact, if the storage layer is comprised of high-speed fibrous absorbent gelling materials, such as FIBERSORB, the storage layer may be relatively poor at transporting fluids in the X-Y plane, but very good at transporting fluids in the Z-direction. In such an embodiment, the acquisition/distribution layer is believed to function by spreading the fluids out on top of the storage layer, and the storage layer quickly takes these in in the Z-direction.

(The term "Z-direction", as used herein, is an orientation with respect to the absorbent article 20 of the present invention if the absorbent article 20 is placed in a Cartesian coordinate system in its flat, laid out condition of FIG. 1 so that the garment surface 20b of the absorbent article 20 lies in the plane formed by the x and y axes (i.e., horizontal). The longitudinal and transverse centerlines l and t of the absorbent article lie in the plane formed by the x and y axes. The "Z-direction" is the direction that is perpendicular to the plane of either surface of the absorbent article 20 when it is in such a flat, laid out configuration.)

The disposable absorbent article of the present invention is believed to have improved containment performance because it has an absorbent core that is capable of immediately taking in and storing exudates that are deposited on it. This improvement in containment performance allows the disposable absorbent article to be made smaller than prior disposable absorbent articles, particularly brief-type incontinent products. As a result, the absorbent articles of the present invention can fit closer to the wearer's body. The absorbent articles of the present invention can fit in the wearer's usual undergarments. The reduction in size of the absorbent article also makes it more comfortable to wear, and more discreet for the wearer.

While particular embodiments of the present invention have been illustrated and described, it would be obvious to those skilled in the art that various other changes and modifications can be made without departing from the spirit and scope of the invention. It is therefore intended to cover in the appended Claims all such changes and modifications that are within the scope of this invention.

What is claimed is:

1. An absorbent article comprising:
   a liquid pervious topsheet;
   a liquid impervious backsheet joined to said topsheet;
   a multiple layer absorbent core positioned between said topsheet and said backsheet, said multiple layer absorbent core comprising at least two pairs of layers, wherein each pair of layers comprises an acquisition/distribution layer and a storage layer, each pair of layers being arranged so that a storage layer is positioned between each acquisition/distribution layer and said backsheet, wherein
      the acquisition/distribution layer in at least one of said pairs of layers has a fluid acquisition/distribution rate of at least about 4 cubic centimeters of synthetic urine per second when said acquisition/distribution layer is placed under a pressure of about 28 grams per square centimeter;
      the storage layer at least partially comprises an absorbent gelling material which can absorb synthetic urine at such a rate that said absorbent gelling material reaches at least about 40% of its absorptive capacity in less than or equal to about 10 seconds; and
   each acquisition/distribution and storage pair of layers is in fluid communication with each adjacent acquisition/distribution and storage pair of layers.

2. An absorbent article comprising:
   a liquid pervious topsheet;
   a liquid impervious backsheet joined to said topsheet;
   a multiple layer absorbent core positioned between said topsheet and said backsheet, said multiple layer absorbent core comprising at least two pairs of layers, wherein each pair of layers comprises an acquisition/distribution layer and a storage layer, each pair of layers being arranged so that a storage layer is positioned between each acquisition/distribution layer and said backsheet, wherein
      the acquisition/distribution layer in at least one of said pairs of layers has a fluid acquisition/distribution rate of at least about 8 cubic centimeters of synthetic urine per second when said acquisition/distribution layer is placed under a pressure of about 28 grams per square centimeter;
      the storage layer at least partially comprises an absorbent gelling material which can absorb synthetic urine at such a rate that said absorbent gelling material reaches at least about 40% of its absorptive capacity in less than or equal to about 10 seconds; and
   each acquisition/distribution and storage pair of layers is in fluid communication with each adjacent acquisition/distribution and storage pair of layers.

3. An absorbent article comprising:
   a liquid pervious topsheet;
   a liquid impervious backsheet joined to said topsheet;
   a multiple layer absorbent core positioned between said topsheet and said backsheet, said multiple layer absorbent core comprising at least two pairs of layers, wherein each pair of layers comprises an acquisition/distribution layer and a storage layer, each pair of layers being arranged so that a storage layer is positioned between each acquisition/distribution layer and said backsheet, wherein the acquisition/distribution layer in at least one of said pairs of layers has a fluid acquisition/distribution rate of at least about 2 cubic centimeters of synthetic urine per second when said acquisition/distribution layer is placed under a pressure of about 28 grams per square centimeter;

the storage layer has a basis weight of between about 320 to about 1,200 grams/square meter and a density of less than or equal to about 0.2 grams per cubic centimeter when the density is measured under a load of 7 grams per square centimeter, and at least partially comprises an absorbent gelling material which can absorb synthetic urine at such a rate that said absorbent gelling material reaches at least about 40% of its absorptive capacity in less than or equal to about 10 seconds; and each acquisition/distribution and storage pair of layers is in fluid communication with each adjacent acquisition/distribution and storage pair of layers.

4. An absorbent article comprising:

a liquid pervious topsheet;

a liquid impervious backsheet joined to said topsheet;

a multiple layer absorbent core positioned between said topsheet and said backsheet, said multiple layer absorbent core comprising four layers which are arranged in the following order beneath the topsheet: a first acquisition/distribution layer; a first storage layer; a second acquisition/distribution layer; and a second storage layer, wherein said first acquisition/distribution layer and first storage layer comprise a first pair of layers and said second acquisition/distribution layer and second storage layer comprise a second pair of layers, and each pair of layers is arranged so that the storage layer in each pair of layers is positioned between the acquisition/distribution layer and the backsheet, wherein:

said first acquisition/distribution layer comprises a nonwoven material having a basis weight of between about 17 to about 135 grams/square meter and a density of between about 0.03 to about 0.05 grams/cubic centimeter;

said first storage layer at least partially comprises an absorbent gelling material which can absorb synthetic urine at such a rate that said absorbent gelling material reaches at least about 40% of its absorptive capacity in less than or equal to about 10 seconds and said first storage layer has a basis weight of between about 20 to about 600 grams/square meter and a density of less than about 0.12 grams/cubic centimeter;

said second acquisition/distribution layer comprises a nonwoven material having a basis weight of between about 70 to about 270 grams/square meter and a density of about 0.03 to about 0.05 grams/cubic centimeter;

said second storage layer at least partially comprises an absorbent gelling material which can absorb synthetic urine at such a rate that said absorbent gelling material reaches at least about 40% of its absorptive capacity in less than or equal to about 10 seconds and said first storage layer has a basis weight of between about 300 to about 1200 grams/square meter and a density of less than about 0.12 grams/cubic centimeter; and said first pair of layers is in fluid communication with said second pair of layers.

5. An absorbent article comprising:

a liquid pervious topsheet;

a liquid impervious backsheet joined to said topsheet;

a multiple layer absorbent core positioned between said topsheet and said backsheet, said multiple layer absorbent core comprising four layers which are arranged in the following order beneath the topsheet: a first acquisition/distribution layer; a first storage layer; a second acquisition/distribution layer; and a second storage layer, wherein said first acquisition/distribution layer and first storage layer comprise a first pair of layers and said second acquisition/distribution layer and second storage layer comprise a second pair of layers, and each pair of layers is arranged so that the storage layer in each pair of layers is positioned between the acquisition/distribution layer and the backsheet, wherein:

said first acquisition/distribution layer comprises a nonwoven material having a basis weight of between about 17 to about 135 grams/square meter and a density of between about 0.03 to about 0.05 grams/cubic centimeter;

said first storage layer at least partially comprises an absorbent gelling material which has a total absorptive capacity of at least about 25 times its dry weight and can absorb at least about 0.8 grams of synthetic urine per second per gram of absorbent gelling material and said first storage layer has a basis weight of between about 20 to about 600 grams/square meter and a density of less than about 0.12 grams/cubic centimeter;

said second acquisition/distribution layer comprises a nonwoven material having a basis weight of between about 70 to about 270 grams/square meter and a density of between about 0.03 to about 0.05 grams/cubic centimeter;

said second storage layer at least partially comprises an absorbent gelling material which has a total absorptive capacity of at least about 25 times its dry weight and can absorb at least about 0.8 grams of synthetic urine per second per gram of absorbent gelling material and said first storage layer has a basis weight of between about 300 to about 1200 grams/square meter and a density of less than about 0.12 grams/cubic centimeter; and said first pair of layers is in fluid communication with said second pair of layers.

6. A multiple layer absorbent core suitable for use in an absorbent article, said absorbent core having a body-facing side and a garment-facing side, said absorbent core comprising:

at least one acquisition/distribution layer having a fluid acquisition/distribution rate of at least about 4 cubic centimeters of synthetic urine per second when said acquisition/distribution layer is placed under a pressure of about 28 grams per square centimeter; and a storage layer for each acquisition/distribution layer positioned closer to said garment-facing side of said absorbent core than said acquisition/distribution layer, said storage layer at least partially comprising an absorbent gelling material which can absorb synthetic urine at such a rate that said absorbent gelling material reaches at least about 40% of its absorptive capacity in less than or equal to about 10 seconds.

7. A multiple layer absorbent core suitable for use in an absorbent article, said absorbent core having a body-facing side and a garment-facing side, said absorbent core comprising:
- at least one acquisition/distribution layer having a fluid acquisition/distribution rate of at least about 8 cubic centimeters of synthetic urine per second when said acquisition/distribution layer is placed under a pressure of about 28 grams per square centimeter; and
- a storage layer for each acquisition/distribution layer positioned closer to said garment-facing side of said absorbent core than said acquisition/distribution layer, said storage layer at least partially comprising an absorbent gelling material which can absorb synthetic urine at such a rate that said absorbent gelling material reaches at least about 40% of its absorptive capacity in less than or equal to about 10 seconds.

8. A multiple layer absorbent core suitable for use in an absorbent article, said absorbent core having a body-facing side and a garment-facing side, said absorbent core comprising:
- at least one acquisition/distribution layer having a fluid acquisition/distribution rate of at least about 4 cubic centimeters of synthetic urine per second when said acquisition/distribution layer is placed under a pressure of about 28 grams per square centimeter; and
- a storage layer for each acquisition/distribution layer positioned closer to said garment-facing side of said absorbent core than said acquisition/distribution layer, said storage layer at least partially comprising an absorbent gelling material having a total absorptive capacity of at least about 25 times its dry weight and can absorb fluids at a rate of at least about 0.8 grams of synthetic urine per gram of absorbent gelling material.

9. A multiple layer absorbent core suitable for use in an absorbent article, said absorbent core having a body-facing side and a garment-facing side, said absorbent core comprising:
- at least one acquisition/distribution layer having a fluid acquisition/distribution rate of at least about 8 cubic centimeters of synthetic urine per second when said acquisition/distribution layer is placed under a pressure of about 28 grams per square centimeter; and
- a storage layer for each acquisition/distribution layer positioned closer to said garment-facing side of said absorbent core than said acquisition/distribution layer, said storage layer at least partially comprising an absorbent gelling material having a total absorptive capacity of at least about 25 times its dry weight and can absorb fluids at a rate of at least about 0.8 grams of synthetic urine per gram of absorbent gelling material.

10. An absorbent article comprising:
- a liquid pervious topsheet;
- a liquid impervious backsheet joined to said topsheet;
- a multiple layer absorbent core positioned between said topsheet and said backsheet, said multiple layer absorbent core comprising at least two pairs of layers, wherein each pair of layers comprises an acquisition/distribution layer and a storage layer, each pair of layers being arranged so that a storage layer is positioned between each acquisition/distribution layer and said backsheet, wherein
  - the acquisition/distribution layer in at least one of said pairs of layers comprises a nonwoven material which has a basis weight of between about 17 to about 270 grams/square meter and a density of between about 0.02 to about 0.1 grams/cubic centimeter when the density is measured under a load of 7 grams per square centimeter and a fluid acquisition/distribution rate of at least about 2 cubic centimeters of synthetic urine per second when said acquisition/distribution layer is placed under a pressure of about 28 grams per square centimeter;
  - the storage layer at least partially comprises an absorbent gelling material which can absorb synthetic urine at such a rate that said absorbent gelling material reaches at least about 40% of its absorptive capacity in less than or equal to about 10 seconds; and
- each acquisition/distribution and storage pair of layers is in fluid communication with each adjacent acquisition/distribution and storage pair of layers.

* * * * *